United States Patent
Kreider et al.

(12)

(10) Patent No.: US 6,200,745 B1
(45) Date of Patent: Mar. 13, 2001

(54) VITRO ASSAY SYSTEM USING A HUMAN CELL LINE FOR TESTING THE EFFECTIVENESS OF ANTI-PAPILLOMA VIRAL AGENTS

(75) Inventors: John W. Kreider, Palmyra, PA (US); Michael G. Angell, Hamburg, MI (US); Loyd H. Smith; Margaret Hitchcock, both of Davis, CA (US); Chris Foster, Carmichael, CA (US); Roslyn Rivkah Isseroff, Sacramento, CA (US)

(73) Assignees: The Penn State Research Foundation, University Park, PA (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 09/195,817

(22) Filed: Nov. 19, 1998

Related U.S. Application Data

(63) Continuation of application No. 09/072,189, filed on May 4, 1998, now abandoned, which is a continuation of application No. 08/684,370, filed on Jul. 19, 1996, now abandoned, and a continuation-in-part of application No. 08/118,948, filed on Sep. 9, 1993, now Pat. No. 5,541,058
(60) Provisional application No. 60/001,350, filed on Jul. 21, 1995.

(51) Int. Cl.[7] .............................. C12Q 1/68; C12Q 1/70
(52) U.S. Cl. .................... 435/5; 435/6; 435/7.1; 435/455; 435/456; 435/325; 435/371
(58) Field of Search ........................ 435/5, 6, 7.1, 455, 435/456, 325, 371

(56) References Cited

PUBLICATIONS

Khan et al., J. Virol., vol. 67, No. 6, pp. 3396–3403, Jun. 1993.*

* cited by examiner

*Primary Examiner*—David Guzo
(74) *Attorney, Agent, or Firm*—Thomas J. Monahan

(57) ABSTRACT

An in vitro method for testing the effectiveness of antiviral agents is provided. The method allows for screening anti-papillomavirus drugs which can interfere with the early and maintenance stages of papillomavirus infection. The method comprises growing epithelial cells susceptible to infection with papillomavirus in a monolayer system and measuring the effectiveness of various agents present in the growing media to interfere with the growth of the virus. The method is free from interferences caused by the regional variability, since the cell cultures are evenly dispersed monolayers.

5 Claims, 22 Drawing Sheets

US 6,200,745 B1

VITRO ASSAY SYSTEM USING A HUMAN CELL LINE FOR TESTING THE EFFECTIVENESS OF ANTI-PAPILLOMA VIRAL AGENTS

CROSS-REFERENCE TO RELATED APPLICATIONS

This is a continuation application of U.S. patent application Ser. No. 09/072,189, filed May 4, 1998, now abandoned, which a continuation of U.S. patent application Ser. No. 08/648,370, filed Jul. 19, 1996, now abandoned, and a continuation-in-part of U.S. patent application Ser. No. 08/118,948, filed Sep. 9, 1993, now U.S. Pat. No. 5,541,058. This application also claims priority of U.S. provisional application Ser. No. 60/001,350, filed Jul. 21, 1995.

GOVERNMENT SPONSORSHIP

This invention was made with Government support under PHS Grant No. AI82687 awarded by the National Institutes of Health. The Government has certain rights in the invention.

FIELD OF INVENTION

This invention relates to a novel in vitro method of testing antiviral activity of various agents. More specifically, it describes a method of testing effectiveness of anti-papillomavirus agents which act early in the infection process. The method is useful in testing effectiveness of existing and potential antiviral drugs, in particular, future drugs directed to treatment of Human Papillomavirus infections.

BACKGROUND OF THE INVENTION

Testing of the antiviral effectiveness of the new and existing agents against Human Papillomavirus are still performed in the in vivo testing involving use of laboratory animals and human subjects. These studies are expensive, time consuming and altered by individual differences among subjects.

A demonstration of efficacy prior to in vivo animal model testing would limit the candidate in vivo agents to the ones with increasing potential for in vivo effectiveness. This is especially important for those newer, more speculative agents for which purer antiviral effects are lacking. In vitro demonstration of efficacy can support a decision for expensive testing in animal model systems. In vitro studies are also useful for exploring drug-virus interactions which are awkward or infeasible in whole animal systems. In vitro testing offers the following advantages: 1) preliminary data on efficacy; 2) rapid turn around time; 3) economy; 4) ability to precisely control environmental conditions; 5) elimination of pharmacokinetics and variability of whole animal systems; and 6) small amounts of drugs are required.

There are no established systems for in vitro papillomavirus testing. There have been some recent, encouraging developments, elsewhere and in our laboratory. Broker's laboratory has recently suggested that the xenograft system, which we originated, might be useful for antiviral testing (S. Dollard, et al., 1992, Gene Dev., 6:1131–1142).

In that one approach, fragments of HPV-11 infected human foreskin tissue is excised from the papillomatous cysts, growing beneath the renal capsule, and the fragments are placed onto a collagen gel "raft" culture. HPV-11 replication continues in the tissue fragment, as cells migrate laterally across the surface of the gel. We have explored the use of this system as a possible target for antiviral testing, and we have found that there is a high degree of regional variability in the extent of cell migration, tissue growth, and HPV-11 replication. We do not believe that this in vitro system is sufficiently consistent or precise to form a basis for tests. Further, since preliminary xenografts are required, the cost of the test includes their preliminary growth for three months, so some of the theoretical advantages of in vitro tests, economy and rapid turn-around are lacking.

Another in vitro system with potential was recently described by Laimins' group (Meyers, et al., 1992, Science, 257:971–973). In this system, human cervical cells, bearing HPV-31b episomal DNA are placed on collagen gel raft cultures and biosynthesis of complete virions occurs in the differentiating cells. It seems likely that this system may also be affected by regional variability.

Many of the disadvantages of the prior art methods of testing antiviral activity are overcome by the method of the present invention which precisely measures antiviral activity without the interferences of the regional variability, since the cell cultures are evenly dispersed monolayers.

SUMMARY OF THE INVENTION

In accordance with the present invention, a new in vitro method of testing of the antiviral activity of the potential agents in the initial stages of papillomavirus infection is presented.

We have recently developed a monolayer cell culture system in which we have conducted antiviral testing. The monolayer is a uniform cell sheet with no regional variability. The system can use, alternatively, two rabbit epithelial cell lines: RK-13, derived from domestic rabbit kidney, and SF1Ep, derived from cottontail epidermis. The cells are planted in vitro, infected with cottontail rabbit papillomavirus CRPV virion, and this is soon followed by a wave of CRPV DNA replication and mRNA synthesis, probably ORFs E6 and E7. Under these conditions, the epithelial cells do not complete cytodifferentiation, a requisite for complete virion synthesis, so the papillomavirus infection is abortive, and the CRPV DNA is lost after 3–5 passages. However, only a few days post-infection is sufficient for antiviral testing.

Testing of the antiviral activity involves exposing cells to the various amount of the agent and measuring the effect on the level of CRPV transcription and cell proliferation/viability.

CRPV infection of an established cottontail epidermal cell line (Sf1Ep) results in the production of CRPV-specific transcripts without concomitant morphological transformation (M. Angell, et al., J. Vir. Meth., 1992, 39:207–216). The most abundant transcripts correspond in size to those of the E6 and E7 open reading frames (ORFs) which are also among the most abundant in domestic and cottontail rabbit papillomas. CRPV RNA production was both time and dose-dependent with RNA production diminishing with decreasing viral dose and increasing culture passage. Infected cultures contain episomal CRPV DNA which did not appreciably change in abundance with time but are significantly reduced with culture passage. All features of in vitro infection, especially RNA production, are inhibited by CRPV-neutralizing but not HPV-11-neutralizing monoclonal antibodies. Much of this inhibition can be attributed to a blockage of viral penetration as indicated by the reduction of CRPV DNA within virus-neutralized cultures. Our data indicate that although CRPV infection of Sf1Ep cells was abortive, it serves as a useful model for analysis of early infection events.

Substituting the neutralizing antibody with an antiviral agent has proven to be a useful way of measuring the effectiveness of the antiviral agents and formed the basis for the novel method of testing the antiviral activity of unknown agents.

OBJECTS OF THE INVENTION

An object of this invention is to provide a novel method of in vitro testing of the antiviral activity of potential antiviral agents.

This and other objects and advantages of the invention over the prior art and a better understanding of its use will become readily apparent from the following description and are particularly delineated in the appended claims.

DETAILED DESCRIPTION OF THE INVENTION

Figure 1:
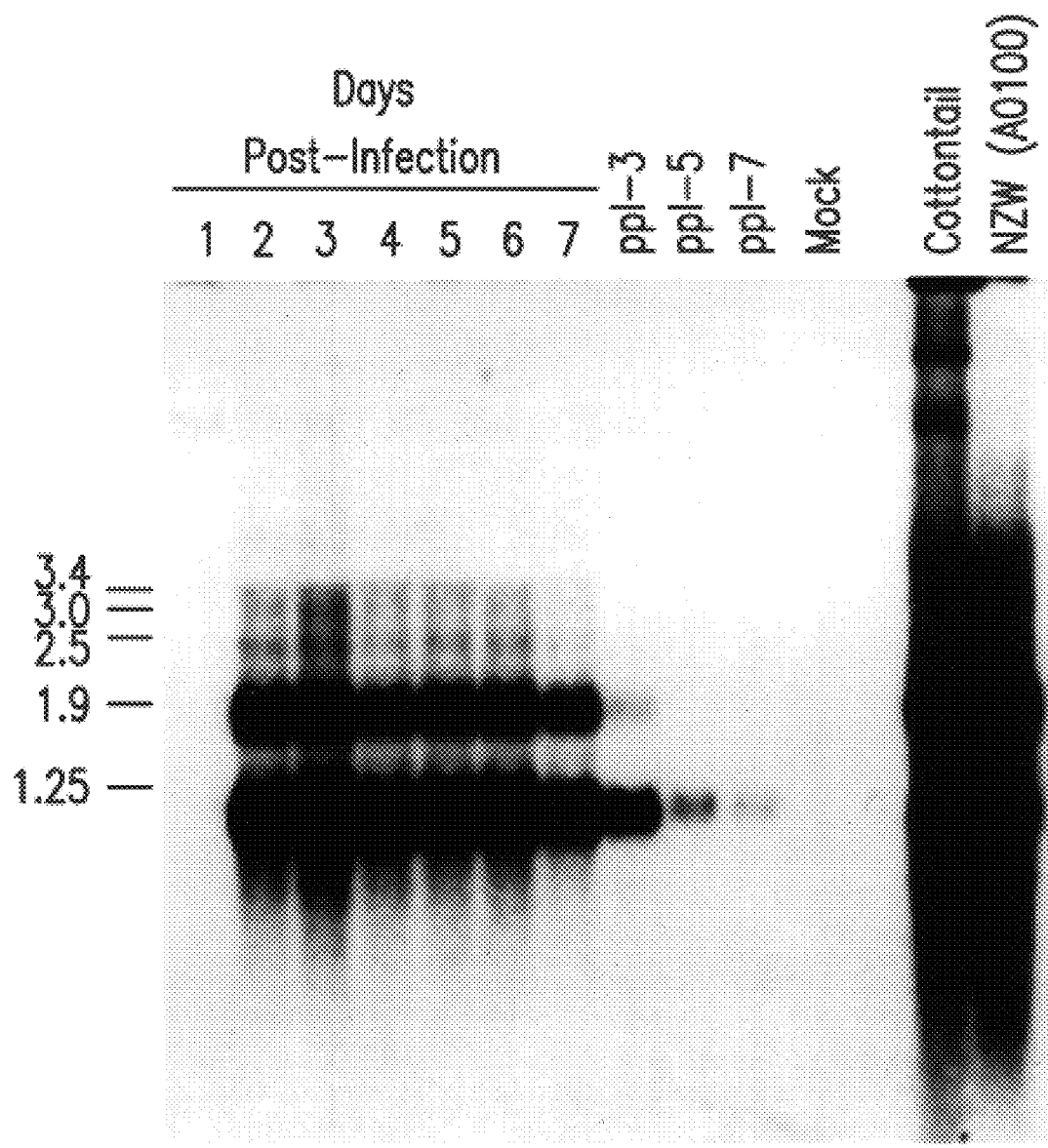
FIG. 1. Northern hybridization of CRPV-infected Sf1Ep cultures. Each sample represents 10 micrograms of total cellular RNA. Samples represent infected cultures days 1–7 after infection as well as cultures passaged (1:2 split every 3rd day) 3, 5 or 7 times after infection (ppI). Cottontail and NZW (A0100) represent RNA isolated from a CRPV-infected cottontail rabbit earskin papilloma cyst and New Zealand White (domestic) rabbit papilloma respectively. Mock indicates RNA isolated from mock infected Sf1Ep cells. Transcript sizes were based on the migration of RNA standard ladders.

The present invention describes the scientific basis as well as preferred way of performing the novel method of testing effectiveness of potential antiviral agents. During the course of detailed studies involving the investigation of the replication of the infected by papillomavirus cells and the effect of various antiviral agents on that process, we have developed a novel method of growing cells in a monolayer cell culture system which allows for conducting the said novel antiviral tests.

A detailed embodiment of this invention involving cells RK-13 and Sf1Ep and CRPV as the studied virus is herein disclosed. Yet another detailed embodiment of this invention involving cultured human keratinocytes cell line is herein disclosed. However it is understood that the preferred embodiment is merely illustrative of the invention which may be embodied in various forms and applications accordingly, specific functional details disclosed herein are not to be interpreted as limiting, especially the type of virus, but merely as a support for the invention as claimed and as appropriate representation for teaching one skilled in art to variously employ the present invention in any appropriate embodiment.

An In Vitro Model System for Studying the Initial Stages of Cottontail Rabbit Papillomavirus CRPV Infection We describe here an in vitro system in which early events in CRPV infection can be studied. This model may be particularly useful in the analysis of additional monoclonal antibodies or other agents which may interfere with viral binding and/or penetration. The system can be used to examine the effectiveness of antiviral agents which act early in the infection process.

Studies with CRPV have been limited due to the lack of an adequate cell culture system. The purpose of the current study was to establish the susceptibility of a cottontail rabbit cell line (Sf1Ep) to infection with CRPV. Our question was whether infection of these cells would result in the production of CRPV-specific RNA and would be inhibitable by virus-neutralizing antibodies.

Previously described in vitro systems for studying CRPV have been based on cell lines derived from CRPV-associated carcinomas (Georges, et al., 1984, J. Virol., 51:530–538; Georges, et al., 1985, J. Virol., 55:246–250; Seto, et al., 1991, J. Invest. Dermatol., 97:327–333 ), on the transfection or exposure of murine cell lines to virus preparations (Watts, et al., 1983, Virology, 125:127–138), or on the infection/transfection of rabbit keratinocytes (Taichman, et al., 1984, J. Invest. Dermatol., 83:2s–6s; Meyers and Wettstein, 1991, Virology, 181:637–646). Among these, only studies utilizing carcinoma cell lines or transformed 3T3s have been analyzed at the transcriptional level. Both rabbit carcinoma and murine cell lines may be inadequate for use in studies involving virus penetration mechanisms. This is due to the species-specificity inherent in papillomavirus infections and to the potential loss of cell surface receptor expression on carcinoma cells. Primary cottontail (*Sylviganus floridanus*) rabbit keratinocytes are the best target cells for such studies because they are the natural host cell. Cottontail skin, in contrast to skin from domestic (*Otyctolagus cuniculus*) rabbits, is permissive for CRPV replication (reviewed by Kreider and Bartlett, 1981, Adv. Cancer Res., 35:81–110). Because of the difficulty in obtaining cottontails and culturing primary rabbit keratinocytes (Breidahl, et al., 1990, Immunol. Cell Biol., 68:119–126), we chose to examine the response of a cottontail epidermal cell line (Sf1Ep) to infection with CRPV.

We demonstrated that infection of Sf1Ep cells with CRPV virion resulted in the dose-dependent production of two major viral transcripts. Infection of these cells did not result in transformation and viral nucleic acids were lost from infected culture upon extended passage. Previously described neutralizing monoclonal antibodies to CRPV (Christensen and Kreider, 1991, Virus Res., 21:169–179), reduced both CRPV penetration and transcription.

At least two, but as many as five virus-specific RNA transcripts (1.25, 2.0, 2.5, 3.0 and 3.5 Kb) were detectable subsequent to in vitro CRPV infection while no viral RNA was found in mock-infected cultures (FIG. 1). Although CRPV transcripts were detectable as early as 17 hours post-infection, viral RNA was maximal between 2–6 days. Transcripts were diminished, beginning seven days post-infection, but were still detectable after 7 passages (21 days) post-infection. Two transcripts, 1.25 and 2.0 Kb, were the most abundant in infected cells. These were also the most abundant in domestic rabbit and cottontail papillomavirus lesions and correspond in size to transcripts from the E7 and E6 ORFs respectively. In both the domestic and cottontail lesions, these transcripts were present in nearly a 1:1 ratio. In in vitro infected cells the 2.0 Kb transcript was approximately 2–4 fold less abundant than the 1.25 Kb transcript (FIG. 1 and data not shown).

Figure 2:
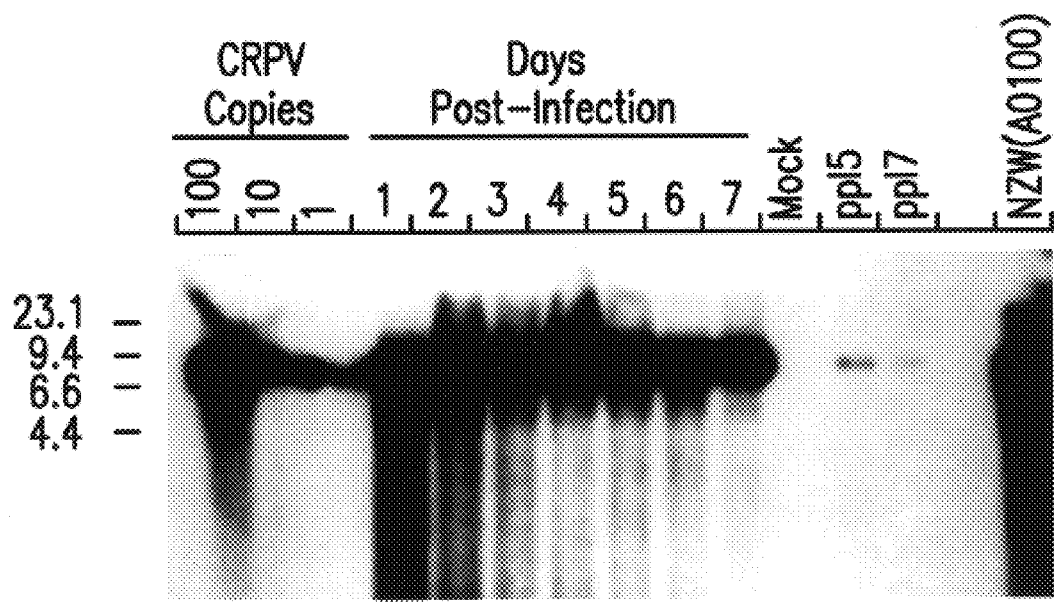
FIG. 2. Detection of CRPV DNA within infected Sf1Ep cultures. Each sample represents 5 micrograms of total cellular DNA from cultures depicted in FIG. 1. All samples were digested with Sal1. Full-length CRPV isolated from pLA2-CRPV was used to reconstruct 1, 10, and 100 copies per diploid genome equivalent (6.55, 65.5, 655 pg respectively). NZW (A0100) and mock represent DNA isolated from a New Zealand White (domestic) rabbit papilloma, and mock-infected cultures, respectively.

Restriction digests of CRPV DNA, isolated from infected cultures, with a single cutting enzyme Sal1 indicated that CRPV was present at between 50 and 100 episomal copies per cell DNA equivalent (FIG. 2). Unlike the RNA transcripts, viral DNA content did not increase with time, and pronounced decreases were seen with passages of infected cultures.

Figure 3:
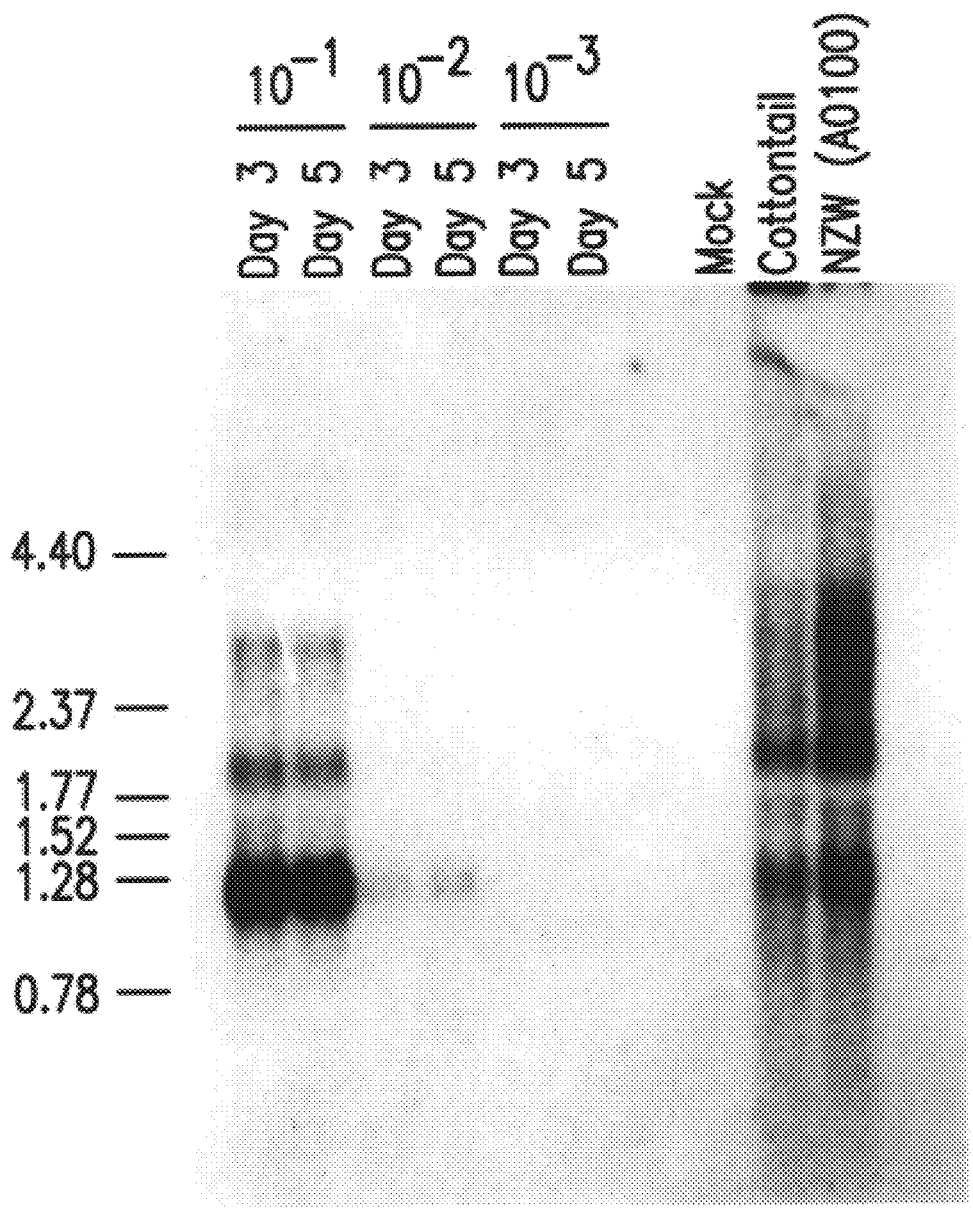
FIG. 3. Northern hybridization of total cellular RNA (10 μg) from Sf1Ep cultures infected with ten fold dilutions of CRPV. Cultures received 200 μl, 20 μl or 2 μl of CRPV stock in 2 ml total volume of media ($10^{-1}$, $10^{-2}$, or $10^{-3}$ respectively). Cottontail and NZW (A0100) represent RNA isolated from a CRPV-infected cottontail rabbit earskin papilloma cyst and New Zealand White (domestic) rabbit papilloma, respectively. Mock indicates RNA isolated from mock infected Sf1Ep cells. Marker positions indicate the migration of RNA standard ladders.
Figure 4:
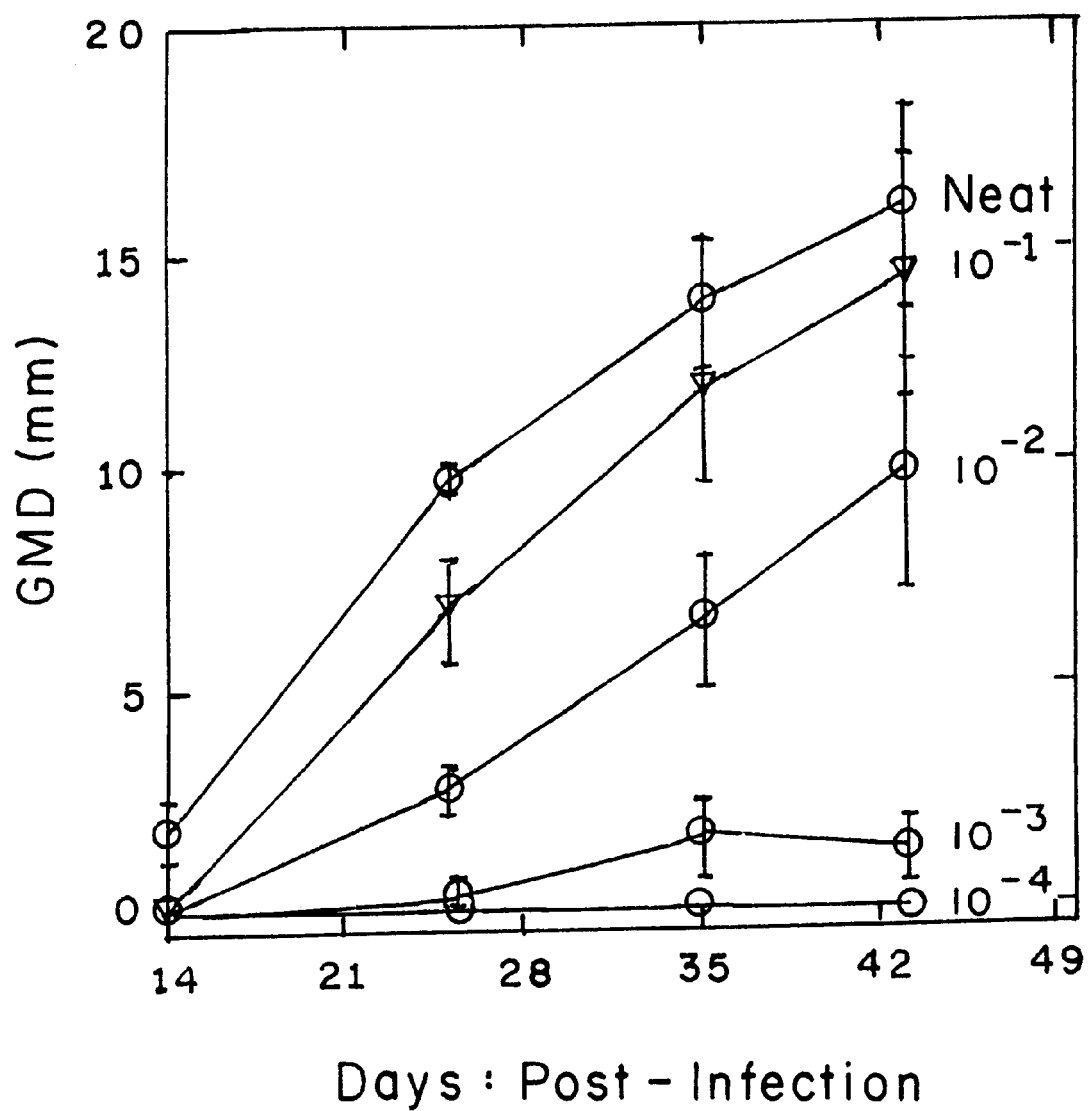
FIG. 4. Rabbit papilloma growth resulting from infection with serial dilutions of CRPV stock. Measurements are expressed as the geometric mean diameter of the lesion. Papillomas were generated with 50 μl of 10-fold serial dilutions of CRPV as in Materials and Methods.

To determine if the amount of viral RNA produced was a reflection of the CRPV copy number within infected cells, we examined the effect of using ten fold serial dilutions of viral stock in the in vitro infection of Sf1Ep cells. CRPV viral RNA was most abundant in cultures infected with a $10^{-1}$ dilution (200 μl) of viral stock. A dilution of $10^{-2}$ produced detectable amounts of RNA while a dilution of $10^{-3}$ did not produce viral RNA by 5 days post-infection (FIG. 3). This coincided with the amount of CRPV DNA within these cultures although cultures receiving a $10^{-3}$ dilution contained detectable, but low amounts of DNA (data not shown). These results correlated with the efficiency at which dilutions of the same viral preparation induced lesions in vivo. Lesions induced with a $10^{-1}$ viral dilution appeared earlier than lesions induced with a $10^{-2}$ dilution while those induced with a $10^{-3}$ dilution appeared much later (FIG. 4).

Figure 5:
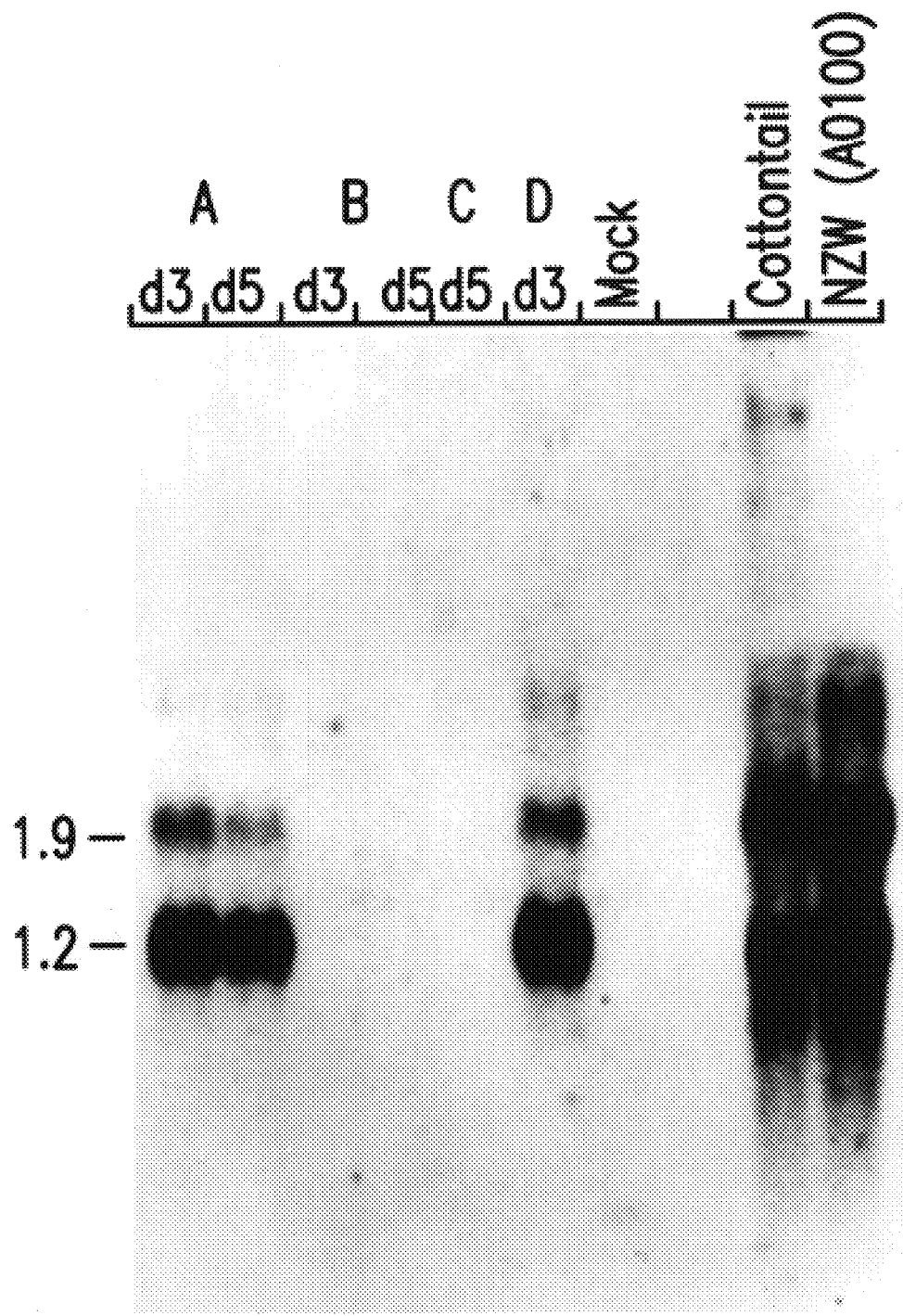
FIG. 5. Northern analysis of cellular RNA (10 μg) isolated from Sf1Ep cultures infected with CRPV preincubated 1 hour with: lane A) media only, lane B) CRPV-neutralizing monoclonal Ab (CRPV4B) 1:10 final dilution, lane C) CRPV-neutralizing monoclonal Ab (CRPV4B) 1:100 final dilution, or lane D) HPV-11 neutralizing monoclonal Ab (H11.B2) 1:10 final dilution. Mock indicates uninfected Sf1Ep cells. Cultures were harvested either 3 days or 5 days after infection. Cottontail and NZW (A0100) represent RNA isolated from a CRPV-infected cottontail rabbit earskin papilloma cyst and New Zealand White (domestic) rabbit papilloma respectively.
Figure 6:
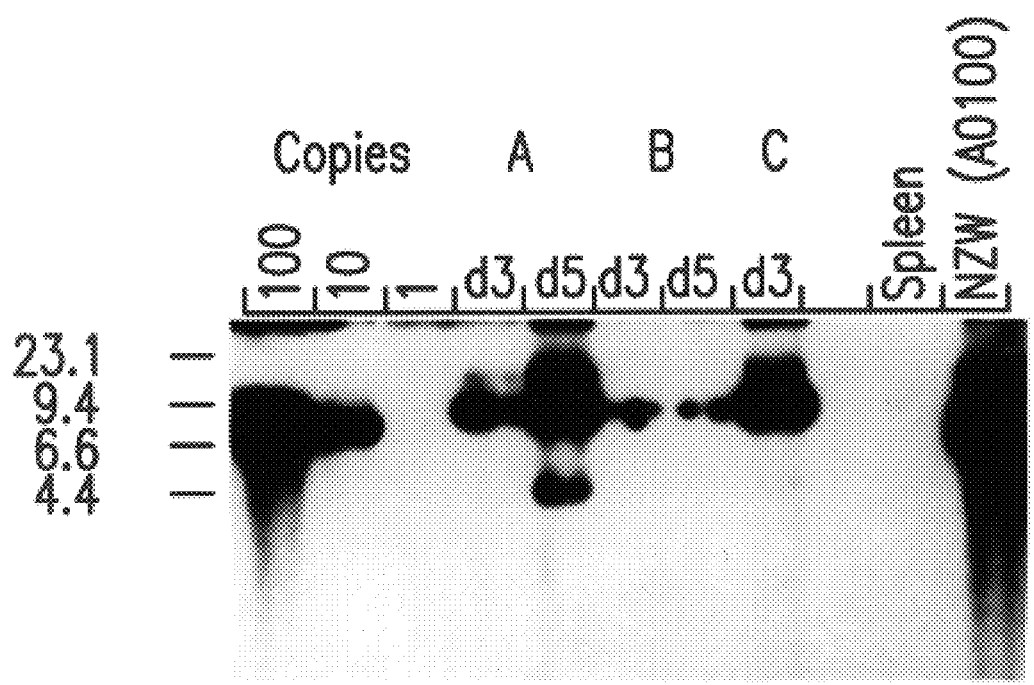
FIG. 6. Southern analysis of Sall-cleaved cellular DNA (5 μg) from Sf1Ep cultures infected with CRPV preincubated with the monoclonal Abs listed in FIG. 5. Lane A) CRPV preincubated with media only; lane B) CRPV preincubated with CRPV4B 1:10 final dilution; lane C) CRPV preincubated with H11.B2 1:10 final dilution. NZW (A0100) indicates CRPV DNA isolated from a New Zealand White (domestic) rabbit papilloma. Spleen represents spleen DNA isolated from a NZW rabbit FIG. 7. Comparison of CRPV transcripts produced in CRPV-infected cultures treated with either PMEG or HPMPC.

Prior incubation of CRPV with a neutralizing monoclonal antibody to CRPV (CRPV4B) inhibited viral RNA production in Sf1Ep cells, while another isotype-matched control antibody (H11.B2), neutralizing for HPV-11, did not (FIG. 5). The initial dilution of the antibody stocks used (1:10) had been previously shown to be neutralizing for HPV-11 or CRPV in vivo. Whereas H11.B2 had no inhibitory activity at this level in our system, CRPV4B was still inhibitory even at a 1:100 dilution. This inhibitory activity did not change with a prolonged culture period of five days. Southern blots of these neutralized cultures show that in most cases persisting CRPV DNA was greatly reduced relative to control and H11.B2 treated cultures (FIG. 6).

The objective of the present study was to establish an in vitro infection system for CRPV in which a marker, in this case RNA production, was dependent upon infection with intact virion. We selected the Sf1Ep cell line for this system for two reasons: a) proper tissue; b) proper host. The source material for this cell line was derived from the epidermis of the natural host, the cottontail rabbit. In addition, this cell line, unlike others, was not previously transformed and contained replicating as well as senescent cell populations.

Other investigators have reported the use of this cell line in CRPV transfection studies (Meyers and Wettstein, 1991, Virology, 181:637–646; Meyers, et at., 1992, J. Virol., 66:1655–1664). These analyses did not involve the use of virion nor was CRPV transcription within transfected cells described. The authors did report transformation-associated changes in transfected cells that represented cell enlargement with the presence of intracytoplasmic inclusions. We occasionally observed this phenomenon within our infected cultures held for at least 30 days without passage. The time course of CRPV RNA production in infected cells was comparable to that reported for abortive infection of bronchial epithelial cells by HPV-1 (Christian, et al., 1987, In: Cancer Cell 5, Cold Spring Harbor Laboratory, New York, pp 165–170). The time delay of approximately 24 hours before the accumulation of abundant viral RNA transcripts may be due to the time required for viral uncoating and/or viral DNA replication. The reason for the decline in viral RNA and DNA amounts upon passage is unclear. Previous studies with HPV-1 infections in vitro indicate that infected cells containing a high copy number of viral DNA, detached from the flask and were lost in passage (Reilly and Taichman, 1987, In: Cancer Cells 5. Cold Spring Harbor Laboratory, New York, pp 159–164). This may also occur here since infected flasks contained significantly more floating/non-viable cells than comparable confluent, uninfected flasks. Likewise, CRPV viral DNA may be underreplicated with respect to the cell genome as was also described for HPV-1.

The most abundant viral transcripts corresponded in size to those of the E6 and E7 ORFs of CRPV. It is interesting, given the abundance of these transcripts, and despite the reported roles of the E6 and E7 ORFs in transformation, that our infected cells were not immortalized and, thus far, have been unable to form tumors in nude mice (unpublished observations). It is also interesting that the greater relative abundance of the 1.25 Kb transcript, consistently seen in infected Sf1Ep cells, has been associated with transcripts from malignant CRPV lesions. In contrast, the levels of the 1.25 and 2.0 Kb transcripts were approximately equal in our benign papilloma controls.

Infection here, using the production of CRPV transcripts as an indicator, was inhibited by monoclonal antibodies that neutralize CRPV infections in vivo. The reduced amounts of DNA present within infected cultures indicate that neutralization most likely occurred by inhibition of viral binding/penetration. The specificity of this event was demonstrated by the fact that isotype-matched monoclonal antibodies which neutralized HPV-11 had minimal effect on CRPV.

Materials and Methods

Cell Lines, Antibodies and Virus

Sf1Ep cells (NBL-11) were obtained through the American Type Culture Collection, Rockville, Md. Cell cultures were maintained in Basal Medium Eagle (GIBCO, Grand Island, N.Y.) supplemented (as complete media) with 1.5 g/l sodium bicarbonate, 10 mM HEPES, 2 mM L-glutamine, 100 $\mu$M non-essential amino acids (Sigma, St. Louis, Mo.), 1 mM sodium pyruvate (GIBCO, Grand Island, N.Y.), 100 U/100 $\mu$g/ml penicillin/streptomycin, and 10% fetal bovine serum. Sf1Ep cells were utilized at passages 80–90. Monoclonal antibodies H11.B2 and CRPV4B were used as culture supernatants containing Clonetic's media (Clonetics Corp., San Diego, Calif.) and 5% keratinocyte conditioned media. These antibodies neutralize HPV-11 and CRPV respectively in vivo (Christensen, et al., 1990, J. Virol., 64:5678–5681; Christensen and Kreider, 1991, Virus Res., 21:169–179). CRPV was obtained as a crude extract from CRPV-infected cottontail earskin implanted subcutaneously in athymic nude mice. CRPV-producing earskin cysts were homogenized in an extraction buffer (1 M NaCl, 20 mM Tris pH 7.4, 2 $\mu$g/ml PMSF) on ice in a Virtis homogenizer at 30K RPM for 5 minutes. The homogenates were centrifuged at 10,000×g for 20 minutes at 4° C. The resulting supernatants were stored at −70° C. Prior to use, viral stocks were quickly thawed, sonicated for 1 minute and centrifuged for 5 seconds.

Nucleic Acid Extraction

For total RNA, cell monolayers were rinsed with Hank's balanced salt solution, without calcium and magnesium (HBSS), and lysed with 4M guanidinium isothiocyanate, 0.1 mM DTT, 0.5% N-lauroylsarcosine, 20 mM sodium acetate pH 5.2. Lysates were layered over a 5.7 M CsCl cushion and centrifuged in a SW55Ti rotor at 35,000 RPM for 20 hr at 18° C. RNA pellets were resuspended in 10 mM Tris-Cl, 5 mM EDTA, 1% SDS followed by subsequent precipitation with 0.3 M sodium acetate and absolute ethanol. DNA was extracted from TE-dialyzed guanidinium/CsCl supernatants by proteinase K digestion (100 $\mu$g/ml) followed by sodium acetate/absolute ethanol precipitation.

Northern Blotting and Hybridization Ten micrograms total cellular RNA was size fractionated by electrophoresis through a 1.4% agarose/8% formaldehyde gel and transferred to Zetaprobe nylon membranes (BioRad, Rockville Center, N.Y.) with 10×SSC (1.5 M sodium chloride, 0.15 M sodium citrate) by capillary action. CRPV genomic sequences were isolated from a pLA2-CRPV construct (Mellon, et al., 1981, Cell, 27:279–288) (obtained from F. Wettstein) by Sal1 digestion and labelled to a specific activity of at least $5\times10^8$ CPM/$\mu$g by random hexamer $^{32}$P-dATP labelling utilizing the Multiprime labelling system (Amersham, Arlington Heights, Ill.). Filters were prehybridized for 30–60 minutes and then hybridized for 24 hrs at 65° C. utilizing a buffer of 7% SDS, 0.5 M $NaH_2PO_4$ pH 7.2, 1 mM EDTA. Filters were then washed at 65° C. 2× with 5% SDS, 40 mM $NaH_2PO_4$ pH 7.2, 1 mM EDTA followed by two additional washes utilizing the same buffer with 1% SDS.

Southern Blotting and Hybridization

Five micrograms of total cellular DNA was digested with Sal1 (CRPV single cutter) using manufacturer's protocol. Digested DNA was sized fractionated on a 0.8% agarose gel and then transferred to Zetaprobe nylon membranes with 0.4 N NaOH after depurination with 0.25 N HCl. Prehybridization and hybridization conditions were as stated above for northern blots.

In Vitro Monolayer Infection System

Two days prior to infection, $5\times10^5$ Sf1Ep cells were seeded into T75 flasks with Eagle's complete media. On the day of infection, the cultures were typically 50% confluent. Flasks were rinsed once with HBSS and infected with 2 mls of a ten-fold dilution of CRPV in Eagle's complete media without serum. Infected flasks were incubated for 2 hours at 37° C./5% $CO_2$ on a slowly rocking platform. After infection, residual inoculum was removed and the flasks rinsed three times with HBSS. Each flask was then fed 10 mls of Eagle's complete media with 10% FBS.

In Vivo CRPV Infection

Two New Zealand White rabbits (Hazelton Research Labs, Denver, Pa.) were infected with 10-fold serial dilutions of the CRPV stock prepared as above. Lesions were initiated by the application of 50 $\mu$l of neat virus or virus diluted with PBS on abraded areas of the dorsal skin. Two sites per dilution were inoculated per rabbit. Tumor measurements were made in three dimensions and the geometric mean diameter (GMD) was calculated per tumor.

Antibody-Mediated Neutralization

Murine monoclonal antibodies neutralizing for CRPV (CRPV4B) or HPV-11 (H11.B2) were generated and analyzed as previously published (Christensen, et al., 1990, J. Virol., 64:5678–5681; Christensen and Kreider, 1991, Virus Res., 21:169–179). Antibody dilutions were made in Eagle's complete media without serum. Prior to infection, 1 ml of 5-fold diluted CRPV stock was incubated with 1 ml of diluted antibody, or media alone, for 1 hr at 37° C. on a rocking platform. After incubation, the antibody-CRPV mixture was added to culture flasks as described above.

Development of the Novel Method of Testing Antiviral Activity by Employing Known Antiviral Agents as the Model Substrate Two well defined (in other experimental systems) agents PMEG (9-(2-phosphonylmethoxy)ethyl-guanine, (E. De Clepcq, et al., 1986, Nature, 323:464–467) and HPMPC ((s)-1-(3-hydroxy-2-(phosphonylmethoxy)propyl)-cytosine, (A. Merta, et al., 1990, Antiviral. Res., 13:209–218) were used to test the effectiveness of this method.

PMEG and HPMPC Treatments

This system uses the Sf1Ep (rabbit cottontail) cell line as an infection target. Recently the use of another rabbit cell line (RK-13) has been included. Both cell lines are cultured in Eagle's Basal Media (with Earls's Salts) containing L-glutanine, Pen/Strep, non-essential amino acids, HEPES, $NaHCO_3$ and fetal bovine serum (10% final volume). For each experiment $5\times10^5$ Sf1Ep cells (or $1\times10^6$ RK-13 cells) are plated in T75 flasks with the above medium. The cells are incubated for 48 hours and then infected for 2 hours with a standard dilution of CRPV viral stock (2 ml volume of virus in the above medium without FBS). After the infection, the cells are rinsed 2× with PBS and 9 mls of culture media (with FBS) are then added per flask. One milliliter of 10×drug (PMEG or HPMPC) solutions are added to the appropriate flasks. For PMEG, 100 $\mu$g, 10 $\mu$g and 1 $\mu$g/ml stocks were used to yield 10 $\mu$g/ml, 1 $\mu$g/ml and 0.1 $\mu$g/ml final concentrations. HPMPC dosages started 100 fold higher than the PMEG due to the reduced toxicity of this compound. Diluent for both drugs, as well as the drug free control consisted of sterile 0.9% saline solution. The infected cells were incubated for 4–6 days post-infection with the media (+/–drug) being changed every other day. Cell counts were performed daily or every other day by directly counting adherent cells using an ocular micrometer at a 100× total magnification. After 4–6 days the cells are harvested by lysis with guanidinium thiocyanate and the nucleic acids extracted by conventional methods as described.

Figure 7:
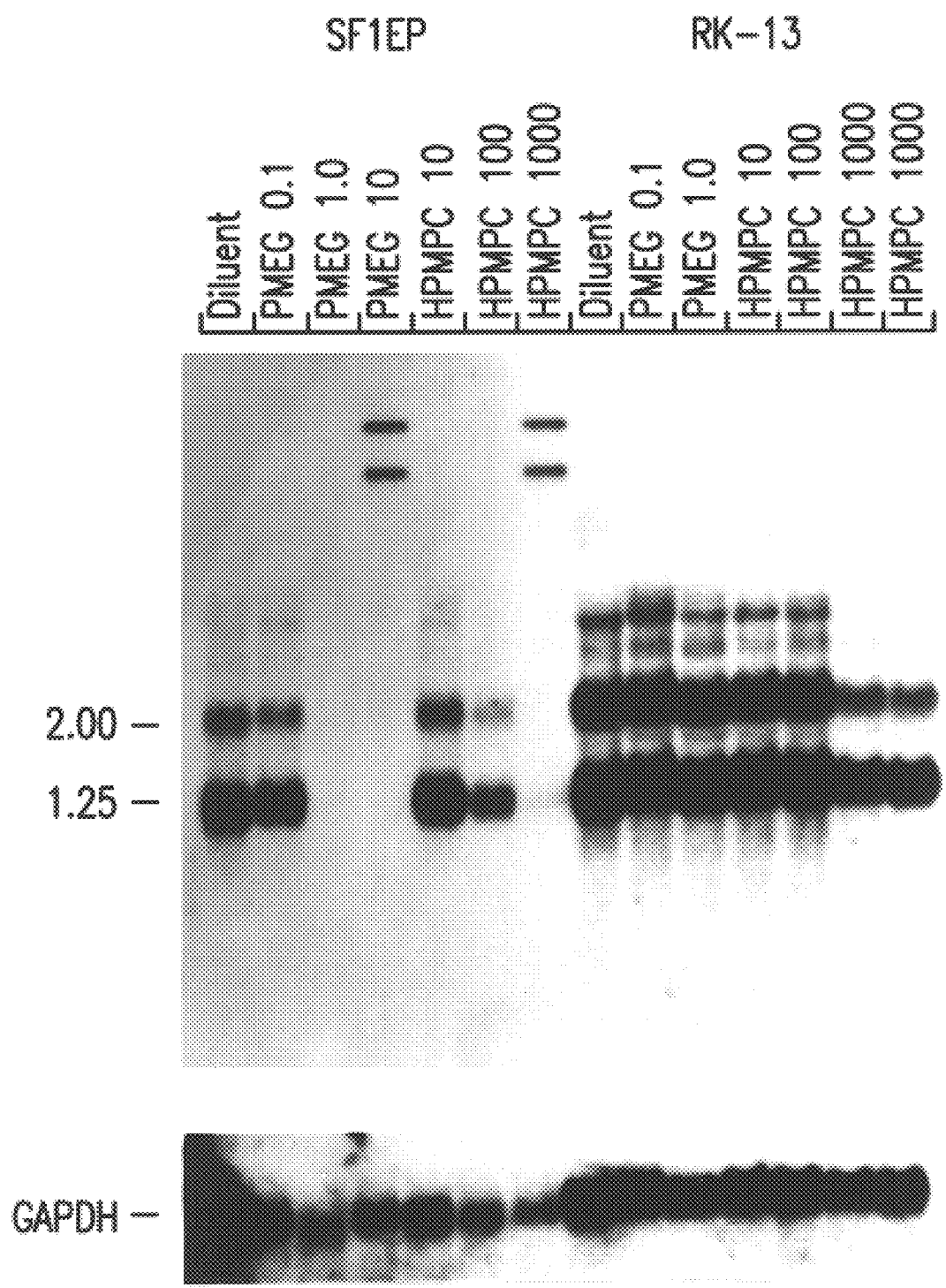
Figure 8A:
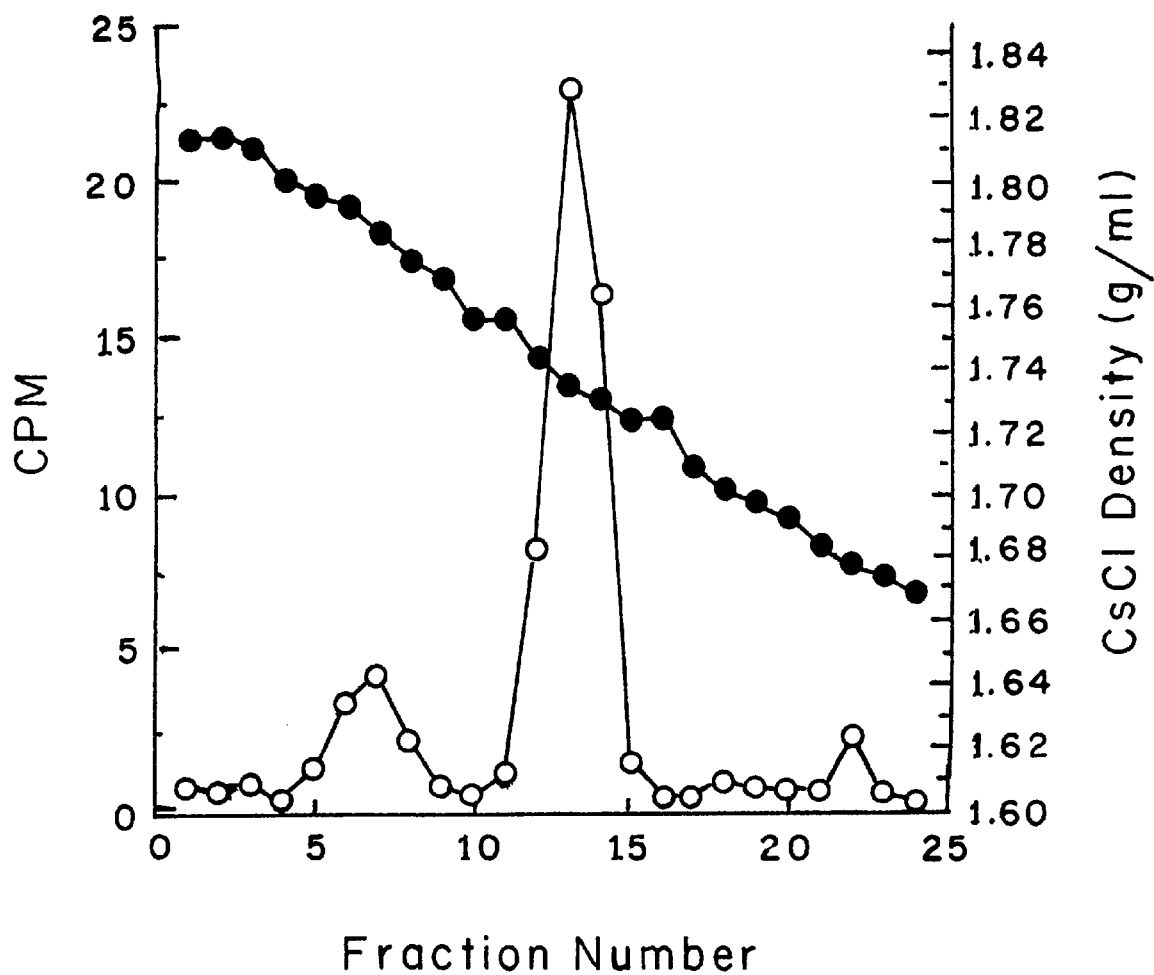
FIG. 8A Presents growth rates from CRPV-infected Sf1Ep cells treated with HPMPC.
Figure 8B:
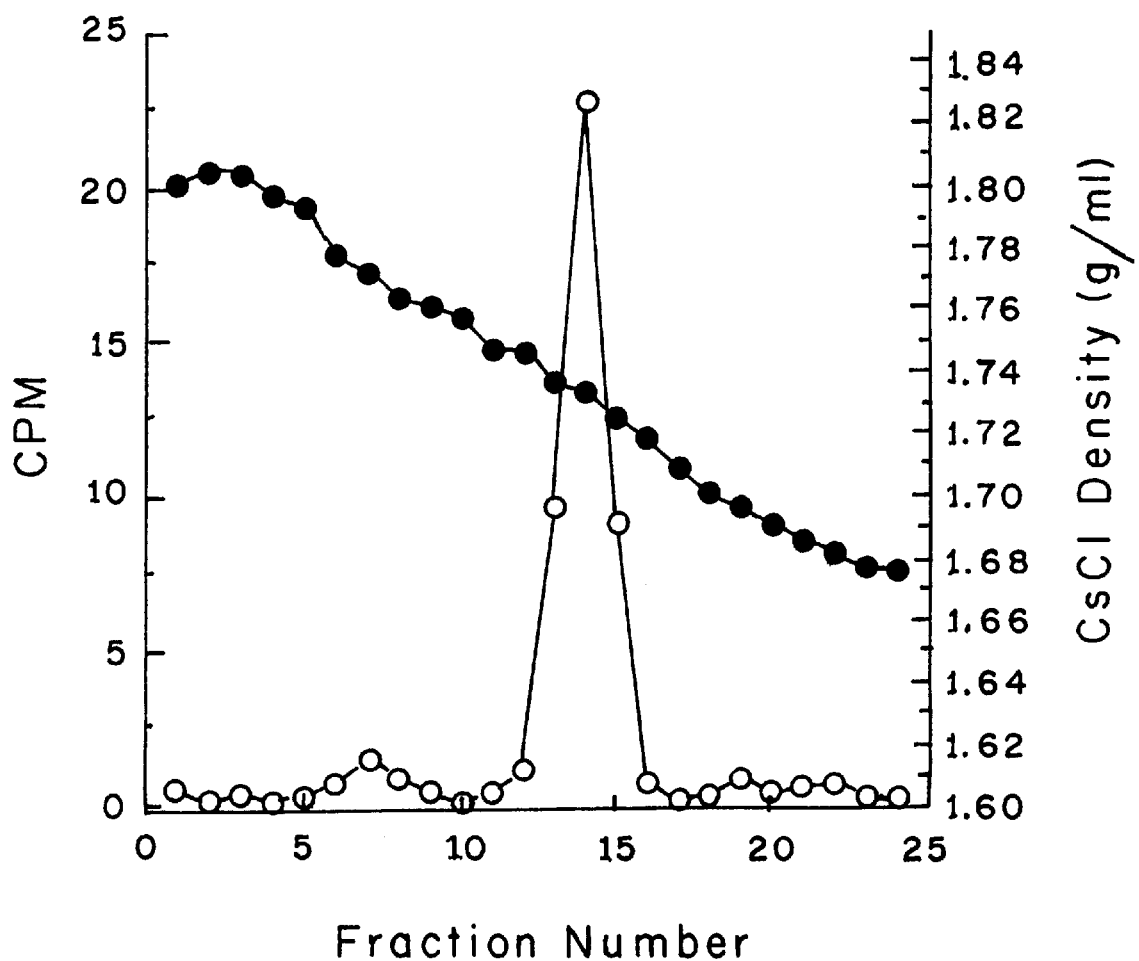
FIG. 8B Presents growth rates from CRPV-infected Sf1Ep cells treated with PMEG.
Figure 8C:
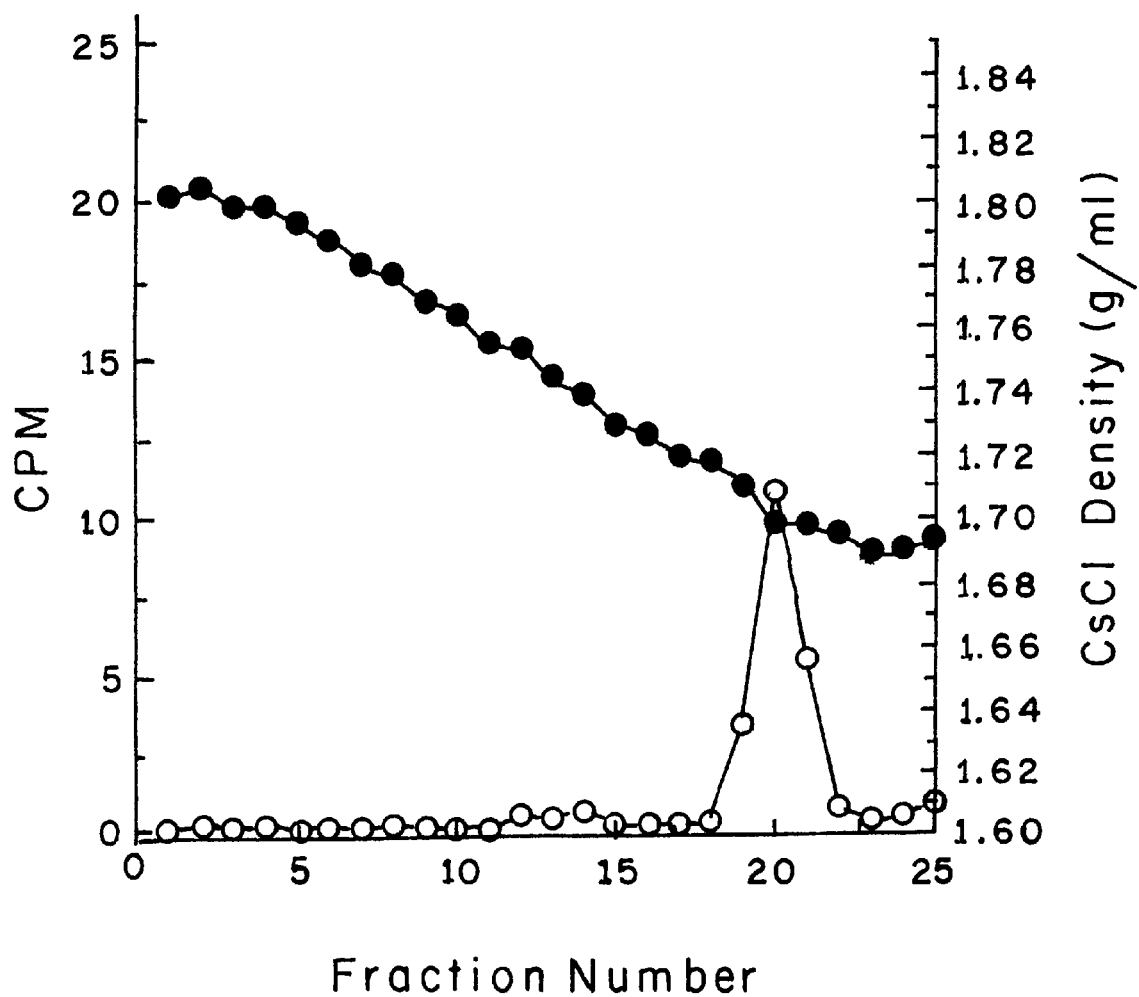
FIG. 8C Presents growth rates of the uninfected Sf1Ep cells treated with HPMPC.
Figure 8D:
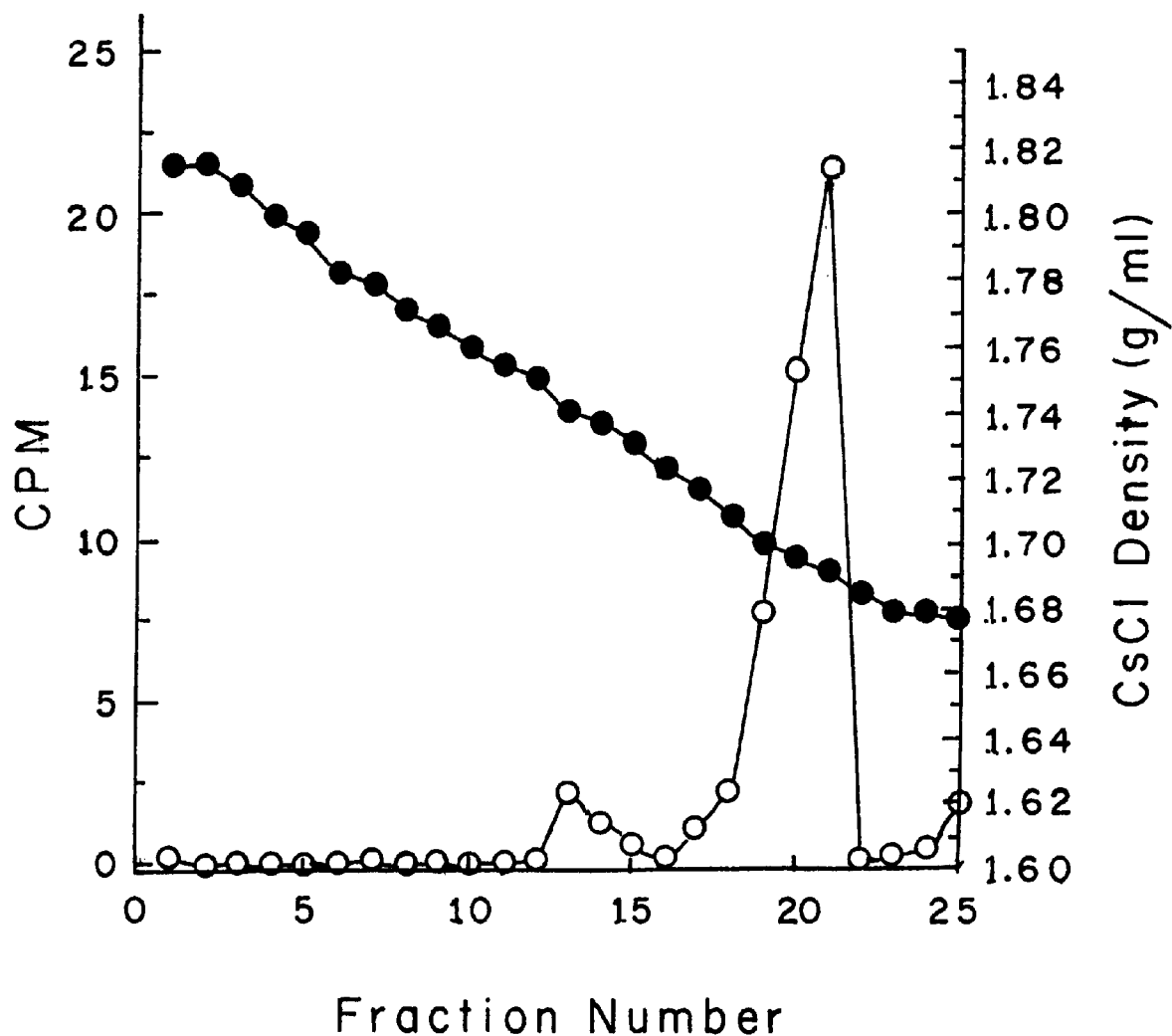
FIG. 8D Presents growth rates of the uninfected RK-13 cells treated with HPMPC.
Figure 9A:
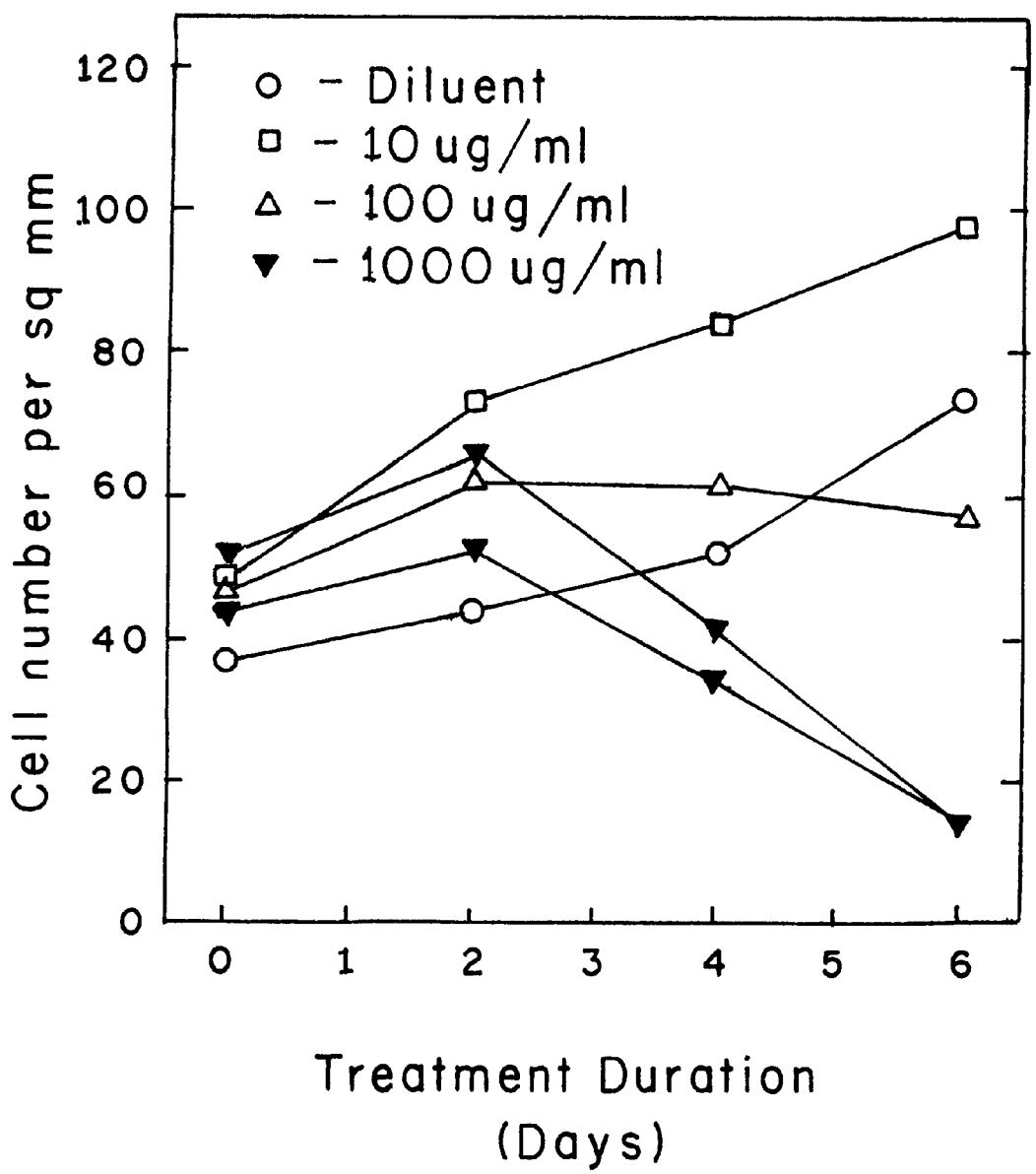
FIGS. 9A and B Present the level of BRdU-labeled (replicated) viral DNA in mock-treated CRPV-infected Sf1Ep cells at 90 hours post-infection.
Figure 9B:
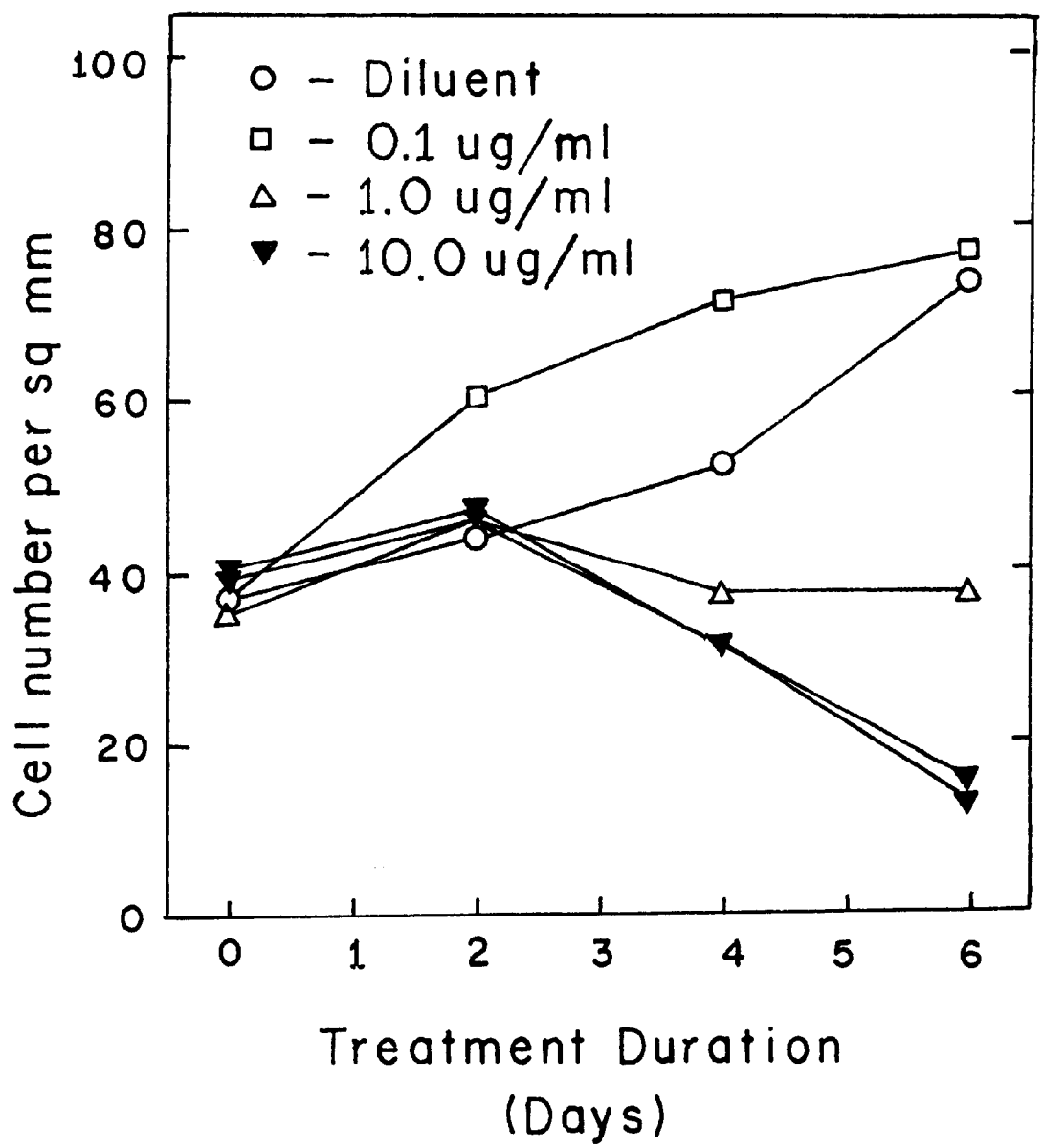
FIGS. 9C and D Present the level of BRdU-labeled (replicated) viral DNA in interferon-treated Sf1Ep cells 130 hours post-infection.
Figure 9C:
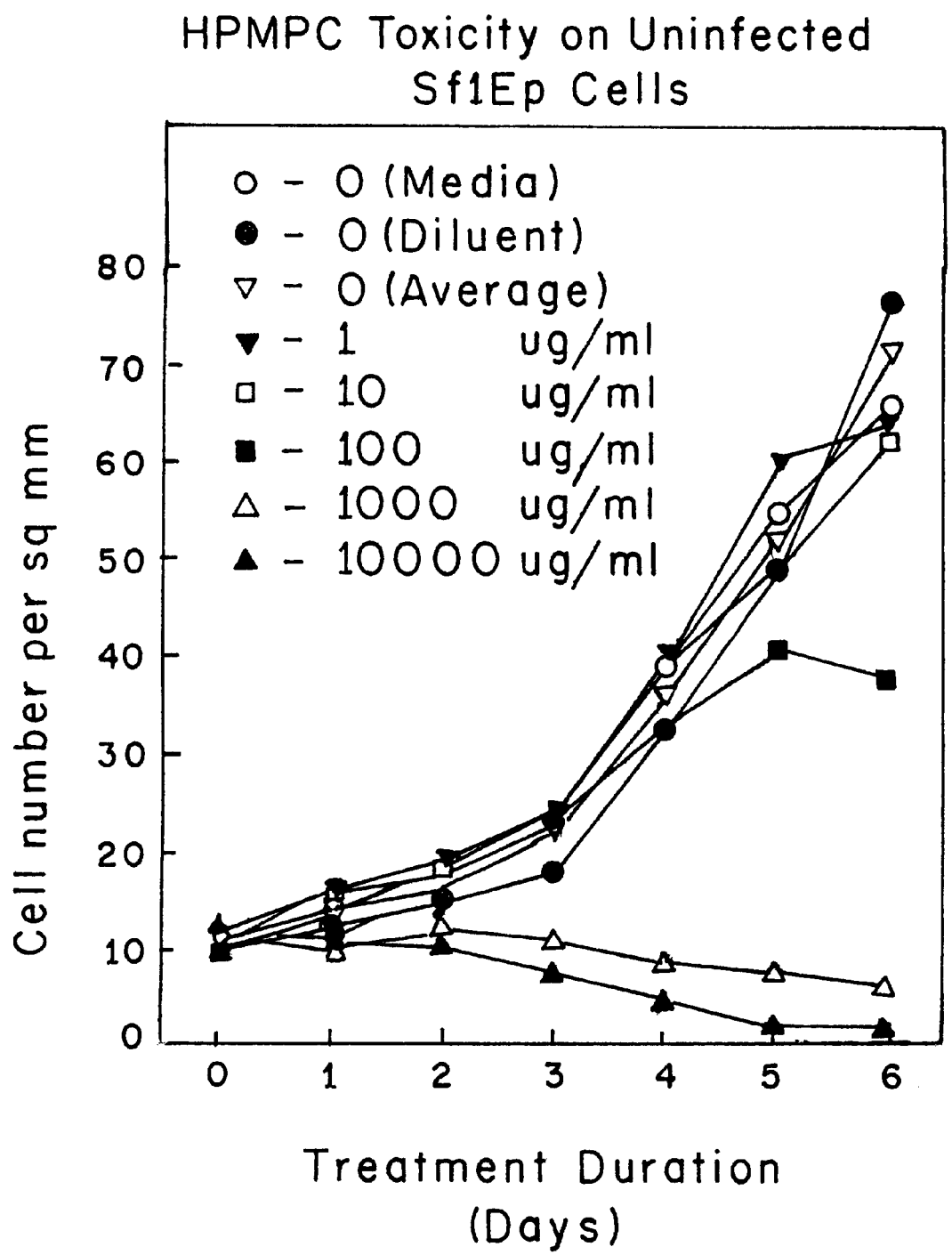
Figure 9D:
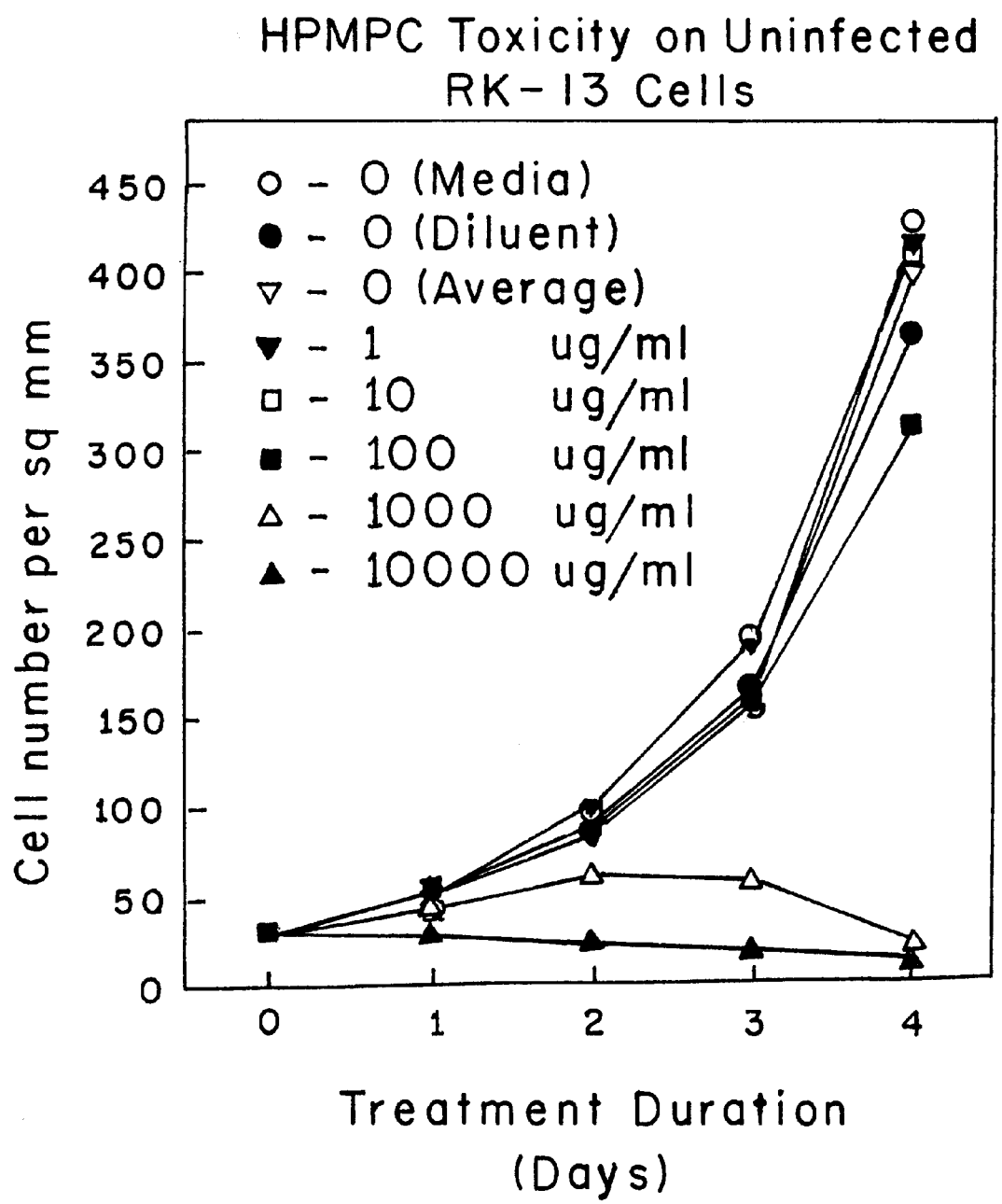

CRPV infected Sf1Ep or RK-13 cells were treated with PMEG (0.1–10 $\mu$g/ml) or HPMPC (10–1000 $\mu$g/ml) for 4–6 days. Effects on CRPV transcription (FIG. 7) and cell proliferation/viability were examined.

Treatment of CRPV-infected Sf1Ep cells with either drug resulted in a reduction of CRPV transcripts at doses found to be growth inhibitory or toxic (FIGS. 8A–D). In contrast, the effects of both drugs on CRPV transcription in infected RK-13 cells were less pronounced even though PMEG and HPMPC at doses of 1.0 $\mu$g/ml and 1000 $\mu$g/ml respectively were found to be toxic to uninfected cells.

The nature of the inhibitory effect of both drugs is unknown, however generalized suppression of RNA transcription is probably not responsible due to the continued expression of GAPDH in the highest treatment groups. We have previously demonstrated that RNA transcript abundance is dependent upon CRPV DNA copy number. Whether drug treatment results in a reduction in CRPV copy number or whether cells containing a high copy number are more sensitive to drug toxicity is unclear.

Effect of Rabbit Fibroblast Interferon (nRaIFN) on CRPV DNA Synthesis In Vitro

We used our CRPV/Sf1Ep infection system to examine the ability of nRaIFN to inhibit CRPV DNA synthesis. CRPV-infected Sf1Ep cells were cultured for up to 6 days in the presence of 1000 U/ml nRaIFN (Lee Biomolecular rabbit fibroblast IFN). At 2, 4, and 6 days post infection, treated and untreated cultures were pulsed with BRdU for 36 hours. The DNA from pulsed cultures was then resolved on a CsCl gradient to separated replicated (BRdU-substituted) and unreplicated DNA. By 90 hours after infection, approximately 93% of the CRPV DNA in IFN treated cells had replicated at least once as compared to 89% in CRPV-infected, IFN-untreated cells. No difference was seen at 130 hours either with approximately 7% of the CRPV DNA being replicated in the IFN treated flask vs. approximately 5% in the untreated flask. No CRPV DNA replication occurred in either group at 6 days post-infection. The drop in CRPV DNA replication between the two time points is most likely due to suppression of cellular DNA synthesis as a result of culture confluency (FIGS. 9A–D).

An In Vitro Model System for Studying the Initial Stages of Human Papillomavirus Infection We describe here an in vitro system for the HPV infection of cultured human keratinocytes and a keratinocyte cell line. This system may be used to characterize titers for HPV infectability, antibody neutralization, and the effectiveness of antiviral agents which act early in the infection process.

Neonatal Human Foreskin Keratinocyte Culture

Processing of neonatal foreskin tissue was performed as previously described in Smith, L. H., Foster C., Hitchcock, M. E., Isseroff R., 1993, Journal of Investigative Dermatology, 101:292–295. Foreskin fragments were cultured at 37° C. in 5% $CO_2$ on a feeder layer of mouse 3T3 fibroblasts treated with mitomycin C (Vidrich, et at., 1988, In Vitro Cell Dev. Biol., 24:188–194; Rheinwald, et al., 1975, Cell, 6:331–334). The cells were grown to 80% confluency. We then cultured outgrowth keratinocytes in Dulbecco's modified Eagle's medium (10% FBS, 10 rg/ml epidermal growth factor, $1\times10^-$ M cholera toxin, 0.4 μg/ml hydrocortisone, 100 μg/ml penicillin, 100 μg/ml streptomycin, 0.25 μg/ml amphotericin). We added fresh medium every other day up to day 7. On day 7 tissue fragments were removed and we changed the medium to a formulation that was serum-free, and containing 0.15 mM calcium (154/HKGS, Cascade Biologics, Portland, Oreg.). The outgrowth keratinocytes were harvested by trypsinization when they reached 50% confluency. The tissue was cryopreserved.

HPV Infection and Neutralization

Cryopreserved outgrowth keratonocytes were removed and were seeded at $1\times10^4$ cells/cm² in 154/HKGS medium and grown to 50% confluency. In some experiments we used the immortalized human keratinocyte cell line HaCat cells (Bonkamp, et al., 1988, J. Cell. Biol., 106:761–771).

HaCat cells were grown in 154/HKGS medium. When the cells had grown to the described confluency, we aspirated the media and then covered the cells with approximately 500 μl of filter sterilized HPV-11 (a 0.2 micron low protein binding filter, Millipore, Bedford, Mass.) diluted in 154/HKGS medium as described below. For neutralization mediated by antibody the appropriate dilutions of test antibody or serum were combined with sufficient shock of virus to ensure identical final concentrations of the virus. These dilutions were incubated for 1 hour at 37° C. and then added to the cultured cells. We added fresh medium at day 3 and at day 6 we removed the medium and harvested the total RNA from each well using TriReagent (Molecular Research Center, Cincinnati, Ohio).

Detection of Spliced HPV-11 and Cellular β-Actin mRNAs by RT-PCR

We show infection of the cultured human keratinocytes and HaCat cells after 6 days by the HPV by reverse transcriptase-polymer chain reaction (RT-PCR). Using RT-PCR we measured spliced HPV-11 mRNA species using donor/acceptor nucleotides 847/3325 (Smith, L. H., Foster C., Hitchcock, M. E., Isseroff R., 1993, Journal of Investigative Dermatology, 101:292–295). The primers used in these experiments are listed in Table I.

TABLE I

Reverse Transcriptase and Polymerase Chain Reaction Primers

| Location in Nested Set | Genomic Nucleotide Numbers | Nucleotide Sequence (5' → 3') |
|---|---|---|
| Upstream, outside | 765–787 | tacaagaccttttgctgggcaca (SEQ ID NO: 1) |
| Downstream, outside | 4088–4110 | aaaggcaggaaaatagcacacac (SEQ ID NO: 2) |
| Upstream, inside | 792–812 | atattgtgtgtcccatctgcg (SEQ ID NO: 3) |
| Downstream, inside | 3877–3896 | cagcaatttgtacaggcactac (SEQ ID NO: 4) |
| Upstream, outside | 1578–1587/2029–2039 | gatgacccagatcatgttg (SEQ ID NO: 5) |
| Downstream, outside | 2735–2744/2857–2867 | ggagcaatgatcttgatcttc (SEQ ID NO: 6) |
| Upstream, inside | 2046–2067 | aacaccccagccatgtacgttg (SEQ ID NO: 7) |
| Downstream, inside | 2455–2467/2563–2570 | actccatgcccaggaaggaagg (SEQ ID NO: 8) |

Efficient and sensitive detection of HPV-11 infection in this culture system required the use of nested PCR primer sets and two 30-cycle PCR rounds, although previous studies on human foreskin tissue fragments required a single round of 30 cycles.

HPV-11 cDNA was primed with H11-DO as previously described (Smith, L. H., Foster C., Hitchcock, M. E., Isseroff R., 1993, Journal of Investigative Dermatology, 101:292–295). We used primers H11-DO and H11-VO (0.2 μM final concentration) for 30 cycles of PCR with the following temperature profile: 94° C./30 seconds, 60° C./30 seconds, 72° C./55 seconds with a final extension of 72° C./10 minutes. We then used five percent of the resultant PCR mixture for a second 30 cycles of PCR, primed with H11-VI and H11-DI (0.2 μM final concentration) using the identical temperature profile. The concentration of dNTPs during DNA synthesis and PCR amplification was 0.2 mM. When dUTP was used the concentration of nucleotide was 0.4 mM.

The final amplimer size was 628 bp. This PCR product has been shown to originate from HPV mRNA (Smith, L. H., Foster C., Hitchcock, M. E., Isseroff R., 1993, Journal of Investigative Dermatology, 101:292–295).

In certain experiments, cellular β-actin mRNA was detected simultaneously with HPV-11. The designed nested primers are described in Table I.

For cDNA synthesis primers BA-DO and BA-UO were used with H11-DO and H11-VO respectively in the first 30 cycles, and BA-DI and BA-UI were used with H11-DI and H11-VI in the second 30 cycles. Expected final amplimer size for the primed β-actin fragment was 429 bp.

The GeneAmp Carryover Prevention Kit (Perkin Elmer) was issued in all PCR reactions, and used per the instructions of the manufacturer. Negative control PCR reactions were routinely performed, confirming the absence of contamination events.

We separated the PCR products by agarose-ethidium bromide gel electrophoresis and photographed the resulting separations using polaroid negative film (665 film, Polaroid Corp., Cambridge, Mass.) which gave a negative image that was subsequently processed by a scanning densitometer. We scanned at 632–25 nm using a helium-neon laser scanner with a gelscan XL software (Pharmacia, Piscataway, N.J.).

Optical Density and Neutralization Values

The relative amounts of the HPV-11 and β-actin mRNA PCR amplimers were determined as "Peak Optical Density"

in the following manner. Background OD was determined by scanning film adjacent to the band of interests, and that OD value was subtracted from the measured peak OD of the band. A percent value for neutralization was calculated:

% neutralization=100−[(normalized $POD_N$/normalized $POD_{Ref}$)× 100], where "normalized $POD_N$" is the ratio of peak OD values for the 628 bp- and the 429 bp-bands in a neutralization test, and "normalized $POD_{Ref}$" is the POD values for the 628 bp- and 429 bp-bands in an unneutralized (reference) test.

Nested PCR Primers Enhance Detection

Figure 10A:
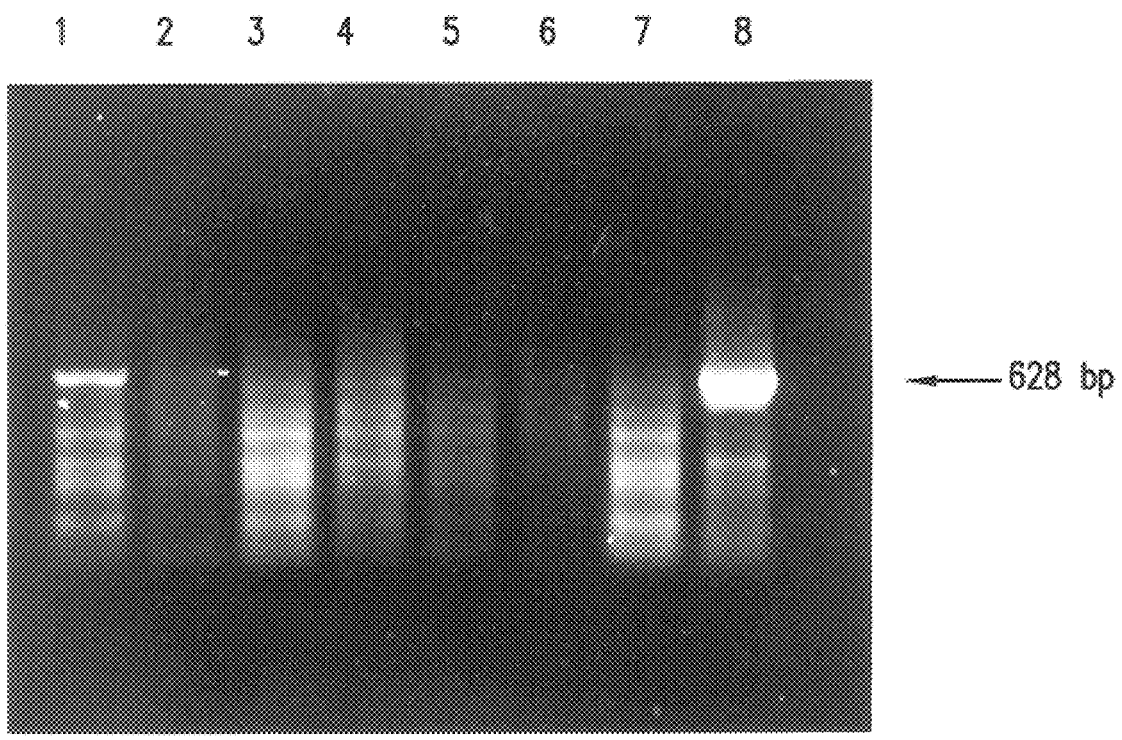
FIG. 10 Presents the ethidium-agarose gel electrophoresis of RT-PCR products from in vitro infectivity assay with HPV-11. A) 30 rounds of PCR amplification. B) 60 rounds of PCR amplification with nested primers. The following lanes contain RT-PCR product derived from in vitro HPV-11 infections using the following virus concentrations: lane 1, $10^{-2}$ dilution ($3\times10^{11}$ particle equivalents/ml); lane 2, $10^{-3}$ dilution ($3\times10^{10}$ particle equivalents/ml); lane 3, $10^{-4}$ dilution ($3\times10^{9}$ particle equivalents/ml); lane 4, $10^{-5}$ dilution ($3\times10^{8}$ particle equivalents/ml); lane 5, $10^{-6}$ dilution ($3\times10^{7}$ particle equivalents/ml); lane 6, $10^{-7}$ dilution ($3\times10^{6}$ particle equivalents/ml); lane 7, $10^{-8}$ dilution ($3\times10^{5}$ particle equivalents/ml).
Figure 10B:
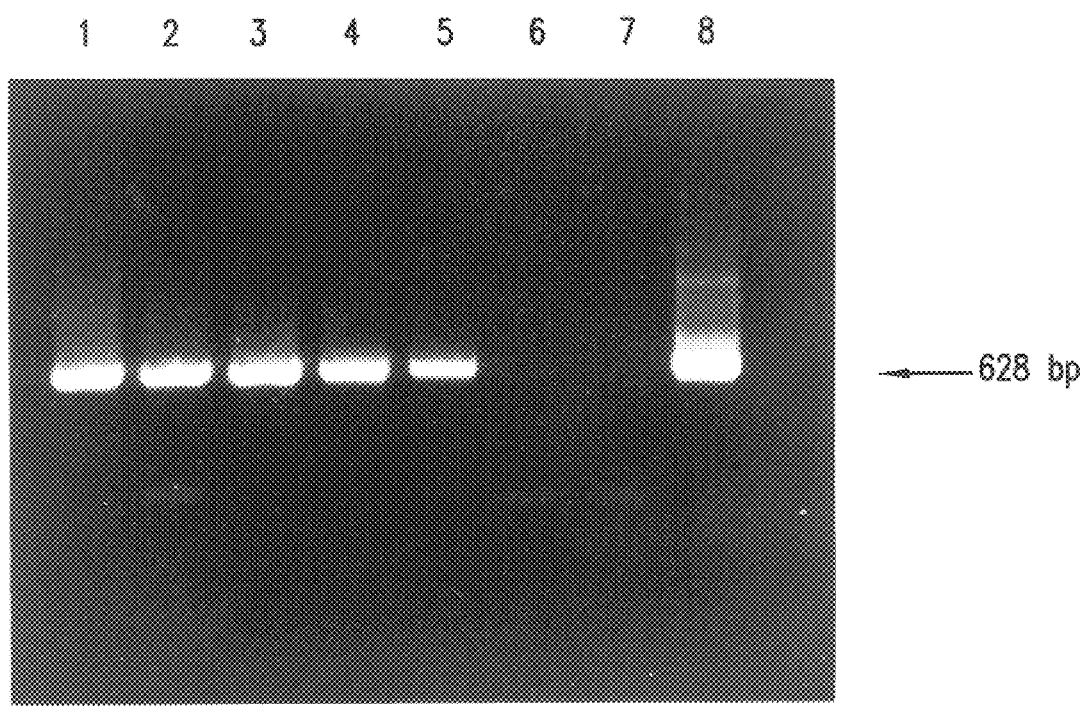

It was previously shown (Smith, L. H., Foster C., Hitchcock, M. E., Isseroff R., 1993, Journal of Investigative Dermatology, 101:292–295) that 30 cycles could be used to detect a PCR amplified fragment. However we find that the results of PCR amplification are poor when 30 cycles are used to amplify mRNA from cultured cell instead of tissue (FIG. 10). Nested primers and 60 cycles of PCR substantially increases detection sensitivity. HPV-11 stock was diluted down to determine the minimal titer required for detection. Under our conditions HPV-11 infection can be detected at a virus concentration of $10^7$ particles per milliliter, equivalent to 500–1000 virion equivalents per cell.

In Vitro RT-PCR Assay of HPV-11 Neutralization

Figure 11:
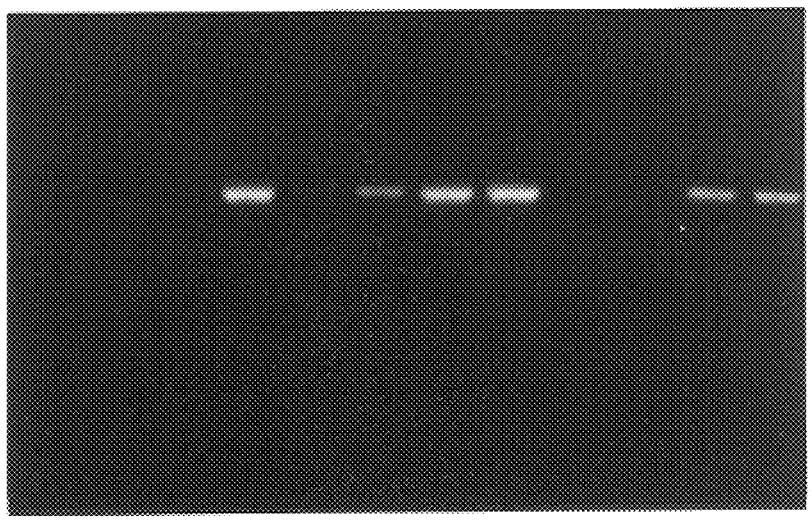
FIG. 11 Presents the in vitro RT-PCR assay demonstrated HPV-11 neutralization by experimental sera. The following antibodies were used in the standard neutralization assay at the indicated concentrations. A) H11.B2 ascites (neutralizing): lane 1, 10-2 dilution; lane 2, $10^{-3}$ dilution; lane 3, $10^{-4}$ dilution; lane 4, no antibody. B) H11.H3 tissue culture supernatant (neutralizing): lane 5, $10^{-2}$ dilution; lane 6, $10^{-3}$ dilution; lane 7, $10^{-4}$ dilution; lane 8, no antibody. C) Rabbit anti-VLP 11-L1: lane 9, $10^{-2}$ dilution; lane 10, $10^{-3}$ dilution; lane 11, $10^{-4}$ dilution; lane 12, no antibody. D) Hyperimmune rabbit irrelevant antibody control: lane 13, $10^{-2}$ dilution; lane 14, $10^{-3}$ dilution; lane 15, $10^{-4}$ dilution; lane 16, no antibody. E) Mouse anti-CRPV ascites (CRPV neutralizing/HPV-11 nonneutralizing): lane 17, $10^{-2}$ dilution; lane 18, $10^{-3}$ dilution, lane 19, $10^{-4}$ dilution; lane 20, no antibody. F) Rabbit pre-immune: lane 21, $10^{-2}$ dilution; lane 22, $10^{-3}$ dilution; lane 23, $10^{-4}$ dilution; lane 24, no antibody.
Figure 11:
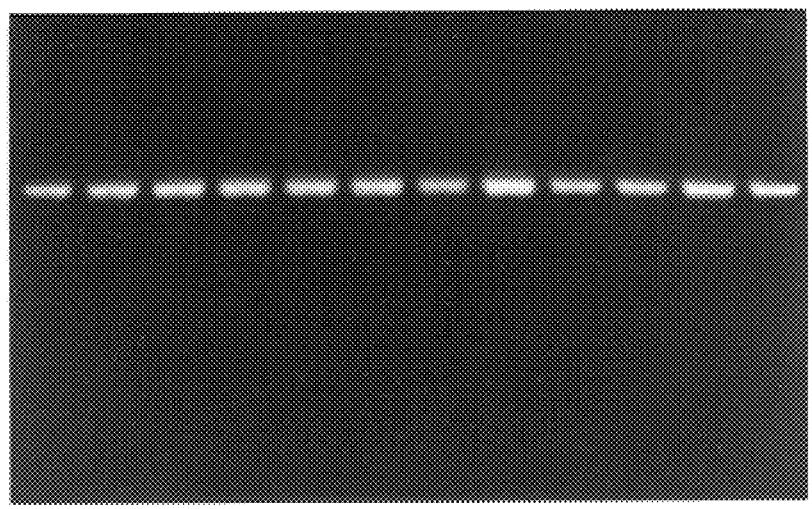
Figure 12:
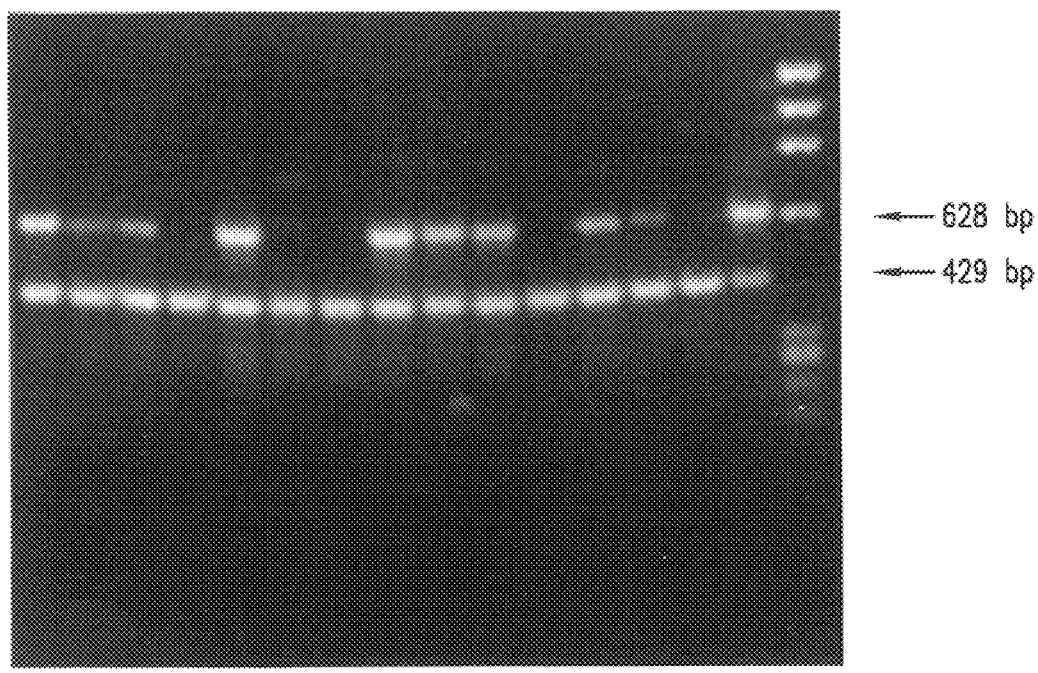
FIG. 12 Presents the RT-PCR analysis demonstrates the effects of virus dilution, antibody neutralization and cell type. RT-PCR products separated by agarose-ethidium gel electrophoresis. Arrows mark positions of 628 bp (HPV-11 mRNA) and 429 bp (β-actin mRNA) amplimers. Lanes 1–7 show assays performed with cultured neonatal foreskin keratinocytes. Lanes 1–4 show results of unnaturalized cultures using tenfold serial dilutions of HPV-11 as follows: lane 1, $10^{-4}$ dilution; lane 2, $10^{-5}$ dilution; lane 3, $10^{-6}$ dilution; lane 4, $10^{-7}$ dilution. Lanes 5–7 show results of assays performed with a 1:100 dilution of HPV-11-neutralizing mouse monoclonal antibody H11.B2 and HPV-11 dilutions as follows: lane 5, $10^{-3}$ dilution; lane 6, $10^{-4}$ dilution; lane 7, $10^{-5}$ dilution. Lanes 8–14 demonstrate results for similar assays as shown in lanes 1–7 except performed using the HaCaT cell line. Lane 15 show a control lane derived from RNA extracted from HPV-11-induced xenograft condyloma. Lane 16 shows $\Phi_\chi 174$ DNA-Hae III digest markers.
Figure 13A:
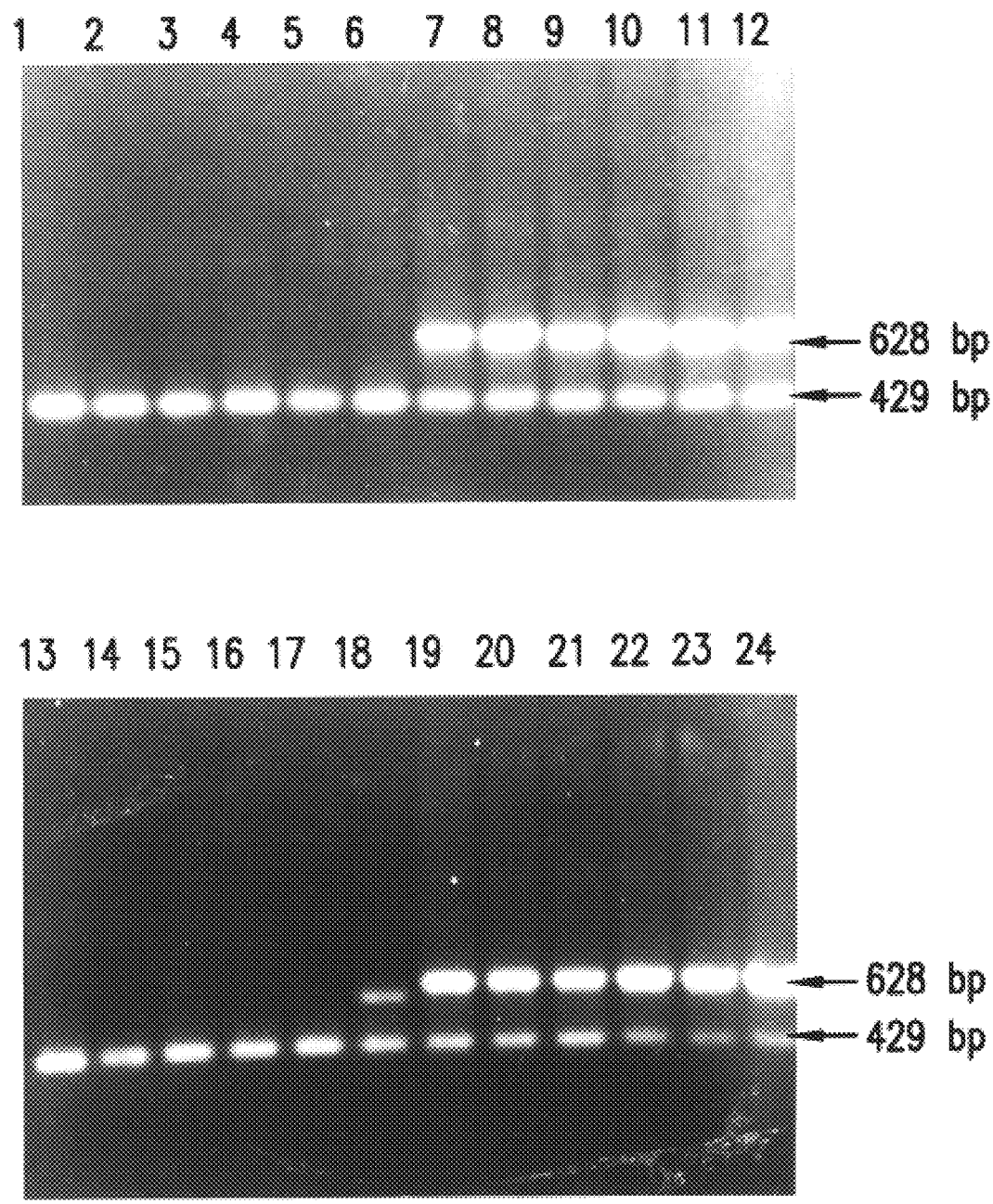
FIG. 13 (Parts A–C) Presents the RT-PCR analysis of HPV-11 neutralization by patient sera. A) Lanes 1–6: patient UCP-1. Lanes 1–3: 1:20 serum dilutions (triplicate experiments); lane 4, 1:40 dilution; lane 5, 1:80 dilution; lane 6, 1:160 dilution. Lanes 7–12, RBD-114. Lanes 7–9, 1:20 serum dilutions (triplicate experiments); lane 10, 1:40 dilution; lane 11, 1:80 dilution; lane 12, 1:160 dilution. Lanes 13–18: RBD-4. Lanes 13–15, 1:20 serum dilutions (triplicate experiments); lane 16, 1:40 dilution; lane 17, 1:80 dilution; lane 18, 1:160 dilution. Lanes 19–24: RBD-115. Lanes 19–21, 1:20 serum dilution (triplicate experiments); lane 22, 1:40 dilution; lane 23, 1:80 dilution; lane 24, 1:160 dilution. B) Lanes 1–6, patient HMC-1, Lanes 1–3, 1:20 serum dilutions (triplicate experiments); lane 4, 1:40 dilution; lane 5, 1:80 dilution; lane 6, 1:160 dilution. Lanes 7–12, patient HMC-3. Lanes 7–9, 1:20 serum dilutions (triplicate experiments); lane 10, 1:40 dilution; lane 11, 1:80 dilution; lane 12, 1:160 dilution. Lanes 13–16; patient UCP-3. Lanes 13–15, 1:20 serum dilutions (triplicate experiments) lane 16, 1:40 dilution; lane 17, 1:80 dilution; lane 18, 1:160 dilution. Lanes 19–24, patient UCP-2. Lanes 19–21, 1:20 serum dilution (triplicate experiments); lane 22, 1:40 dilution; lane 23, 1:80 dilution; lane 24, 1:160 dilution. C) Lanes 1–6, patient UCP-4. Lanes 1–3, 1:20 serum dilutions (triplicate experiments); lane 4, 1:40 dilution; lane 5, 1:80 dilution; lane 6, 1:160 dilution; lane 7, $\Phi_\chi 174$ DNA HAE III digest markers. Lanes 8–13, RBD-107, Lanes 8–10, 1:20 serum dilutions (triplicate experiments); lane 11, 1:40 dilution; lane 12, 1:80 dilution; lane 13, 1:160 dilution. Lane 14, no sample. Lane 15, control from HPV-11-induced xenograft condyloma RNA extract. Lane 16, no sample. Lanes 17–19 derived from uninfected cultures (no virus controls). Lane 20, $\Phi_\chi 174$ DNA Hae III digest makers. Lanes 21–23 derived from HPV-11-infected cultures without neutralizing sera. Lanes 24–32, no sample.
Figure 13B:
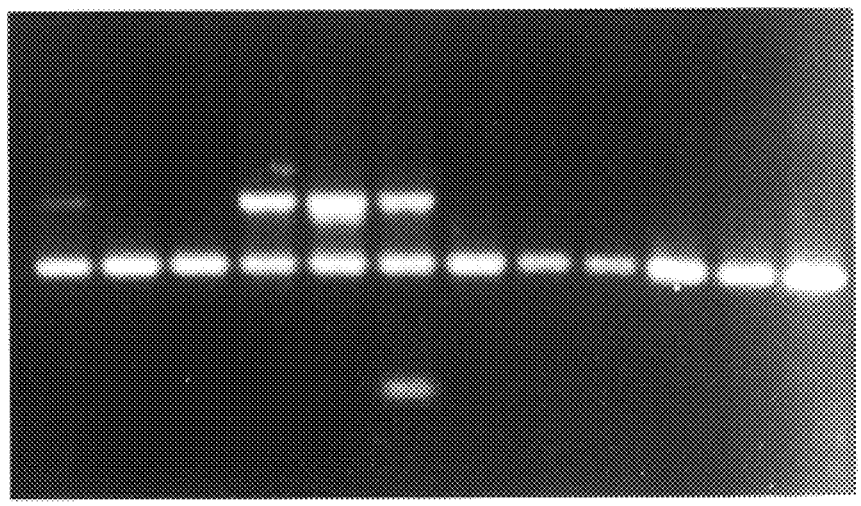
Figure 13B:
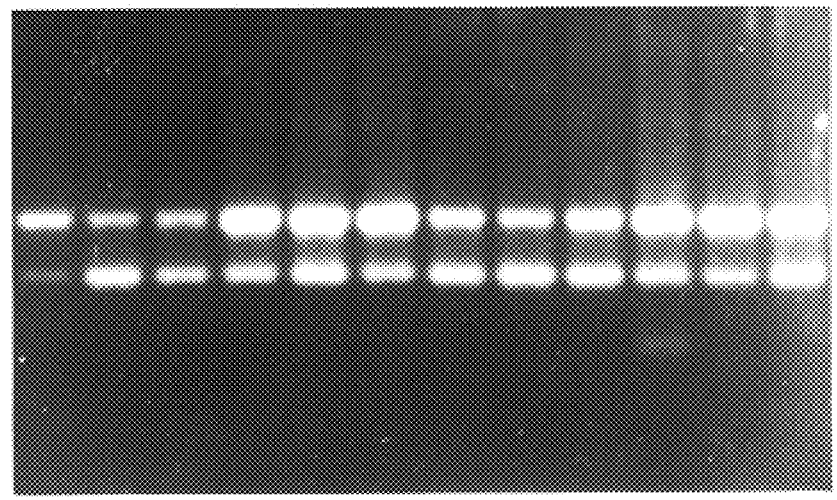
Figure 13C:
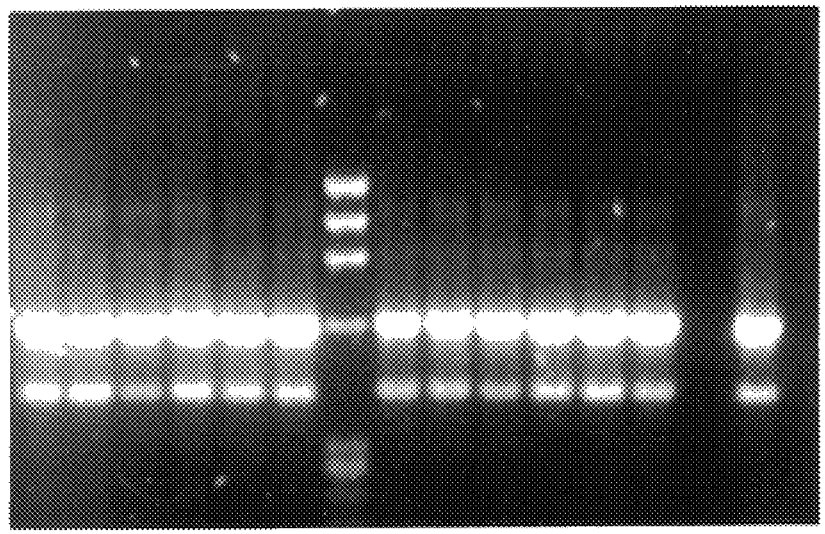
Figure 13C:
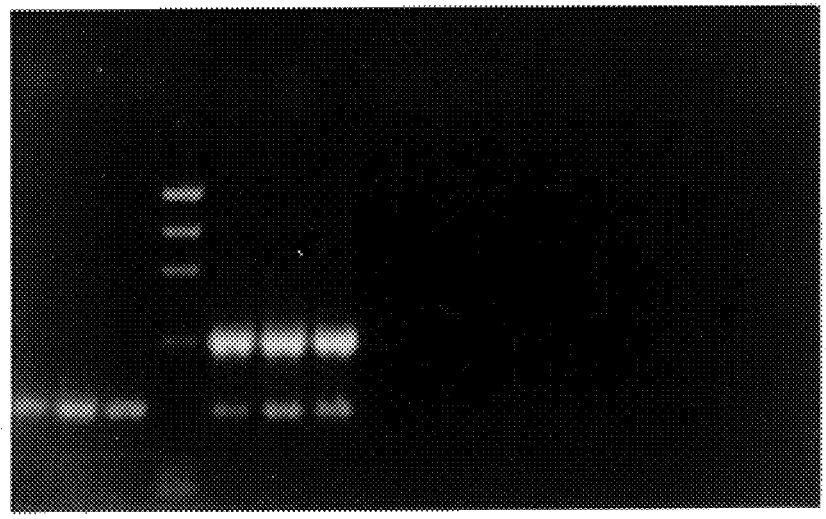

Mouse monoclonal antibodies H11.B2 and H11.H3 have been shown previously to neutralize the ability of HPV-11 to induce condylomata in the athymic mouse xenograft model (Christensen, et al., 1990, J. Virol. 64:5678–5681). These monoclonal antibodies were very active in neutralizing the ability of HPV-11 to induce the HPV-11-spliced mRNA in the in vitro system. As can be seen in FIG. 3, both antibodies could be substantially diluted and still completely inhibit HPV-11 infection. Experimental antisera were also tested for neutralizing activity in this in vitro system. FIG. 11 also shows the results with rabbit sera before and after immunization against HPV-11-like particles producted in a baculovirus vector. The pre-immunization sera had no HPV-11-neutralizing activity. As previously reported using the mouse xenograft HPV-11-neutralization assay, the post-immunization serum was highly active and could inactivate HPV-11 infection even at a dilution of In vitro titration of HPV-11 infectivity and antibody-mediated neutralization was possible using the technique described here. The reliability of this method is affected by several sources of variability. HPV-11 preparations may vary in their content of infectious particles and therefore dilutional titration is required to chose the appropriate virus dilution at which antibody-mediated neutralization can be observed consistently. FIG. 12 (lanes 5–7) shows the results of HPV-11 neutralization with a fixed dilution of the HPV-11-neutralizing mouse monoclonal antibody H11.B2. Although neutralization was observed at the $10^{-4}$ and $10^{-5}$ virus dilutions, it was not observed at the $10^{-3}$ dilution. A similar calibration would be required when using new or previously untested HPV-11 stockes in this assay. For the HPV-11 prepration described here, a $10^{-4}$ dilution (approximately $10^9$ particle equivalents/ml) was selected for neutralization studies using patient sera.

Spurious absence of the 628-bp PCR product representing the spliced HPV-11 mRNA could arise from loss of cellular RNA, failure of cDNA synthesis, or faulty PCR. To control for these potential sources of variability, an internal control mRNA was needed that was expected to be present in all cellular RNA extracts. The spliced β-actin mRNA was chosen because both genomic and cDNA sequences were available (GenBank) and because several exon-exon splice junctions (Nakajima-Iijima, S., et al., 1985, Proc. Nat'l. Acad. Sci., USA 82:6133–6137) could be utilized to derive specific primers for RT-PCR. Dideoxysequence analysis of this amplimer following cloning into the pCR2 vector, using previously described methods (Smith, L. H., et al., 1993, J. Invest. Dermatol., 101:292–295) demonstrated the 429-bp β-actin amplimer with an additional 27 bp of flanking DNA located to the downstream side of primer BA-DI (Hitchcock, unpublished observation). The source of this flanker remains to be determined but all RT-PCR generated the same size amplimer for all reactions. We refer to this β-actin amplimer as the 429-bp fragment to reflect the size of the β-actin specific sequence. FIG. 12 demonstrates that the appearance of the 429-bp RT-PCR product provided a clear marker for recovery of spliced β-actin mRNA, confirming in those cases where the 628-bp HPV-11 mRNA product was absent due to neutralization that the result was not due to loss of RNA or failure of RT-PCR.

Routine cultivation of secondary cultures of neonatal human foreskin keratinocytes was also regarded as a source of variability for this work. The source of keratinocytes for each preparation was different and keratinocyte cultures sometimes showed variable growth characteristics. A continuous human keratinocyte cell line (HaCaT) was tested as a possible surrogate for cultured neonatal foreskin keratinocytes. FIG. 12 (lanes 8–14) demonstrates that HaCaT cells can be substituted for neonatal human foreskin keratinocytes in both the infectivity titration and antibody-mediated neutralization assays with nearly identical results.

RT-PCR Analysis of HPV-11 Neutralization by Patient Sera

The HPV-11 antibody-mediated neutralization assay was used to screen for neutralizing activity within patient sera. In these studies, conditions were adopted to optimize detection of neutralization as revealed by the data of FIG. 12 (HaCaT cells were used and the HPV-11 dilution was $10^{-4}$). The sera were screened in triplicate at a 1:20 dilution, and single determinations were performed at dilutions of 1:40, 1:80, and 1:160. Sera from two patients with laryngeal papillomatosis, four patients with ongoing genital condyloma, and four random blood donors were tested. The laryngeal papillomatosis patients (HMC-1 and HMC-3) both had tissue typed as HPV 6/11 (Viratype) and both their sera had been shown to bind HPV-11 virions by enzyme-linked immunosorbent assay and to neutralize HPV-11 infectivity in the mouse xenograft assay (Christensen, N. D., et al., 1992, J. Gen. Virol., 1261–1267). Of the four condyloma patients, two (UCP-1 and UCP-2) had been tissue typed for HPV-11 using PCR with consensus primers (Lungu, O., et al., 1992, Mol. Cell Probes, 6:145–152). Tissues from the other two condyloma patients were unavailable for testing.

FIG. 13 represents the results of these assays on patient sera, showing the RT-PCR products separated by agarose-ethidium electrophoresis. The presence of the 429-bp PCR amplimer resulting from the cellular β-actin mRNA eliminated spurious loss of RNA or failure of RT/PCR as an explanation for disappearance of the HPV-11 628 bp amplimer in neutralized cultures. Quantitative data from these gels, obtained by scanning densitometry, is displayed in Table II.

TABLE II

Calculation of HPV-11 Neutralization
Data Using Scanning Densitometry

| Serum Source | Dilution | n | POD 628 bp | POD 429 bp | % Neutralization ± Sd[b] | $NT_{50}$[c] |
|---|---|---|---|---|---|---|
| HMC-1 | 1:20 | 3 | 0.06 ± 0.09[a] | 0.49 ± 0.05[a] | 89 ± 20 | 1:20 |
|  | 1:40 | 1 | 0.54 | 0.45 | 0 | — |
|  | 1:80 | 1 | 0.61 | 0.50 | 0 | — |
|  | 1:160 | 1 | 0.49 | 0.48 | 0 | — |
| HMC-3 | 1:20 | 3 | 0 ± 0 | 0.38 ± 0.10 | 100 ± 0 | — |
|  | 1:40 | 1 | 0 | 0.51 | 100 | — |
|  | 1:80 | 1 | 0 | 0.45 | 100 | — |
|  | 1:160 | 1 | 0 | 0.49 | 100 | >1:160 |
| UCP-1 | 1:20 | 3 | 0 ± 0 | 0.44 ± 0.01 | 100 ± 0 | — |
|  | 1:40 | 1 | 0 | 0.45 | 100 | — |
|  | 1:80 | 1 | 0 | 0.37 | 100 | — |
|  | 1:160 | 1 | 0 | 0.45 | 100 | >1:160 |
| UCP-2 | 1:20 | 3 | 0.40 ± 0.06 | 0.41 ± 0.03 | 38 ± 10 | <1:20 |
|  | 1:40 | 1 | 0.61 | 0.37 | 0 | — |
|  | 1:80 | 1 | 0.63 | 0.35 | 0 | — |
|  | 1:160 | 1 | 0.54 | 0.41 | 0 | — |
| UCP-3 | 1:20 | 3 | 0.31 ± 0.03 | 0.27 ± 0.13 | 33 ± 30 | <1:20 |
|  | 1:40 | 1 | 0.65 | 0.37 | 0 | — |
|  | 1:80 | 1 | 0.62 | 0.43 | 0 | — |
|  | 1:160 | 1 | 0.64 | 0.34 | 0 | — |
| UCP-4 | 1:20 | 3 | 0.73 ± 0.04 | 0.46 ± 0.02 | 3 ± 5 | <1:20 |
|  | 1:40 | 1 | 0.86 | 0.58 | 0 | — |
|  | 1:80 | 1 | 0.85 | 0.56 | 0 | — |
|  | 1:160 | 1 | 0.84 | 0.53 | 0 | — |
| RBD-4 | 1:20 | 3 | 0 ± 0 | 0.30 ± 0.04 | 100 ± 0 | — |
|  | 1:40 | 1 | 0 | 0.31 | 100 | — |
|  | 1:80 | 1 | 0 | 0.28 | 100 | 1:80 |
|  | 1:160 | 1 | 0 | 0.24 | 45 | — |
| RBD-107 | 1:20 | 3 | 0.70 ± 0.02 | 0.42 ± 0.03 | 4 ± 3 | <1:20 |
|  | 1:40 | 1 | 0.80 | 0.48 | 0 | — |
|  | 1:80 | 1 | 0.81 | 0.53 | 0 | — |
|  | 1:160 | 1 | 0.78 | 0.43 | 0 | — |
| RBD-114 | 1:20 | 3 | 0.57 ± 0.05 | 0.41 ± 0.01 | 19 ± 20 | <1:20 |
|  | 1:40 | 1 | 0.62 | 0.38 | 0 | — |
|  | 1:80 | 1 | 0.63 | 0.38 | 0 | — |
|  | 1:160 | 1 | 0.52 | 0.31 | 0 | — |
| RBD-115 | 1:20 | 3 | 0.45 ± 0.03 | 0.25 ± 0.03 | 47 ± 6 | <1:20 |
|  | 1:40 | 1 | 0.48 | 0.18 | 23 | — |
|  | 1:80 | 1 | 0.43 | 0.13 | 0 | — |
|  | 1:160 | 1 | 0.45 | 0.12 | 0 | — |

[a]Mean SD.
[b]% Neutralization: see Materials and Methods.
[c]$NT_{50}$ neutralization tier (highest twofold serial dilution resulting in at least 50% neutralization).

Four sera (HMC-1, HMC-3, UCP-1, and RBD-4) had significant neutralizing activity at the 1:20 dilution; two sera (HMC-3 and UCP-1) showed complete neutralization even at the 1:160 dilution. $NT_{50}$ values (the most diluted serial two-fold dilution capable of at least 50% neutralization) differed dramatically between sera.

The median percent neutralization values (at the 1:20 dilution) for sera with $NT_{50}$ values less than 1:20 (UCP-2, UCP-3, UCP-4, RBD-107, RBD-114, AND RBD-115, each measured in triplicate) were significantly difference from the median percent neutralization values from sera with $NT_{50}$ values of 1:20 or greater (HMC-1, HMC-3, UCP-1, and RBD-4, also each in triplicate), using the Mann-Whitney test ($p<0.0001$). Sera with $NT_{50}$ values of less than 1:20 (determined in triplicate) were regarded as non-neutralizing. These data demonstrate that scanning densitometry of the RT-PCR products yields peak OD values for the 628-bp and 429-bp bands that are reproducible, and that statistical comparison of calculated percent neutralization values for different groups of data is possible.

We believe that these data indicate that this system will be useful to study selected antivirals for their effects on early stages of papillomavirus infections, especially viral DNA synthesis and expression.

The method provides a mean to conduct a primary screen of potential drugs candidates as it is likely that this stage of the infection is critical to viral persistence in the papillomavirus-infected cell, it is a more relevant target for antivirals than is the formation of complete virions in differentiated cells. This later phase occurs sparsely in most human lesions and not at all in "inapparent" or latent infections, which are the likely source of lesion recurrences post-treatment.

The invention described herein provides a novel model for studying antiviral effectiveness of various agents. We believe that this in vitro system is sufficiently consistent or precise to form a basis for a testing method.

The present invention offers a method which precisely measures antiviral activity without the interferences of the regional variability of organ cultures.

Thus, while we have illustrated and described the preferred embodiment of my invention, it is to be understood that this invention is capable of variation and modification, and we, therefore, do not wish or intend to be limited to the precise terms set forth, but desire and intend to avail myself of such changes and alterations which may be made for adapting the invention of the present invention to various usages and conditions. Accordingly, such changes and alterations are properly intended to be within the full range of equivalents and, therefore, within the purview of the following claims. The terms and expressions which have been employed in the foregoing specification are used therein as terms of description and not of limitation, and thus there is no intention in the use of such terms and expressions of excluding equivalents of features shown and described or portions thereof, it being recognized that the scope of the invention is defined and limited only by the claims which follow.

Thus is described my invention and the manner and process of making and using it in such full, clear, concise, and exact terms so as to enable any person skilled in the art to which it pertains, or with which it is most nearly connected, to make and use the same.

What is claimed is:

1. An in vitro method of testing antiviral activity of a potential antiviral agent comprising the steps of:

growing cells capable of producing a Human Papillomavirus in a monolayer system wherein said cells do not complete cytodifferentiation post-infection;

infecting the cells with intact Human Papillomavirus virions;

introducing the potential antiviral agent to the growing culture of the infected cells; and measuring expression of nucleic acids in the cells growing in the presence and absence of the potential antiviral agent as a measure of said potential antiviral agent's effectiveness to interfere with the growth of the virus in infected cells.

2. The method in claim 1 wherein the said growing cells are cultured human keratinocytes.

3. The method of claim 1 wherein the said papillomavirus is Human Papillomavirus-11.

4. The method of claim 1 wherein said antiviral activity is measured within a few days post-infection with the virus.

5. The method of claim 1 wherein said potential antiviral agent's effectiveness to interfere with the growth of the virus is measured at an early stage of said infection with Human Papillomavirus.

* * * * *

SEQUENCE LISTING

<160> NUMBER OF SEQ ID NOS: 8

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: PCR primer

<400> SEQUENCE: 1
tacaagacct tttgctgggc aca                                                23

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: PCR primer

<400> SEQUENCE: 2
aaaggcagga aaatagcaca cac                                                23

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: PCR primer

<400> SEQUENCE: 3
atattgtgtg tcccatctgc g                                                  21

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: PCR primer

<400> SEQUENCE: 4
cagcaatttg tacaggcact ac                                                 22

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: PCR primer

<400> SEQUENCE: 5
gatgacccag atcatgttg                                                     19

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: PCR primer

<400> SEQUENCE: 6
ggagcaatga tcttgatctt c                                                  21

<210> SEQ ID NO 7
<211> LENGTH: 22

```
<212> TYPE: DNA
<213> ORGANISM: Artificial Sequence
<220> FEATURE:
<223> OTHER INFORMATION: Description of Artificial Sequence: PCR primer

<400> SEQUENCE: 7
aacaccccag ccatgtacgt tg                                              22

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: PCR primer

<400> SEQUENCE: 8
actccatgcc caggaaggaa gg                                              22
```